(12) United States Patent
Carney et al.

(10) Patent No.: US 7,473,534 B2
(45) Date of Patent: Jan. 6, 2009

(54) ASSAYS FOR CANCER PATIENT MONITORING BASED ON LEVELS OF EPIDERMAL GROWTH FACTOR RECEPTOR (EGFR) EXTRACELLULAR DOMAIN (ECD) ANALYTE, ALONE OR IN COMBINATION WITH OTHER ANALYTES, IN BODY FLUID SAMPLES

(75) Inventors: Walter P. Carney, North Andover, MA (US); Peter J. Hamer, Reading, MA (US); Allan Lipton, Hershey, PA (US); Kim Leitzel, Hummelstown, PA (US); Suhail M. Ali, Hershey, PA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 97 days.

(21) Appl. No.: 10/375,371

(22) Filed: Feb. 27, 2003

(65) Prior Publication Data

US 2003/0219842 A1 Nov. 27, 2003

Related U.S. Application Data

(60) Provisional application No. 60/360,678, filed on Mar. 1, 2002, provisional application No. 60/429,487, filed on Nov. 27, 2002.

(51) Int. Cl.
*G01N 33/574* (2006.01)
(52) U.S. Cl. .......................... 435/7.23; 435/4
(58) Field of Classification Search ................ 435/7.23, 435/4
See application file for complete search history.

(56) References Cited

U.S. PATENT DOCUMENTS

| | | | |
|---|---|---|---|
| 4,946,778 | A | 8/1990 | Ladner et al. |
| 5,122,464 | A | 6/1992 | Wilson et al. |
| 5,223,409 | A | 6/1993 | Ladner et al. |
| 5,344,760 | A | 9/1994 | Harvey et al. |
| 5,401,638 | A | 3/1995 | Carney et al. |
| 5,403,484 | A | 4/1995 | Ladner et al. |
| 5,427,908 | A | 6/1995 | Dower et al. |
| 5,516,637 | A | 5/1996 | Huang et al. |
| 5,571,698 | A | 11/1996 | Ladner et al. |
| 5,580,717 | A | 12/1996 | Dower et al. |
| 5,604,107 | A | 2/1997 | Carney et al. |
| 5,658,727 | A | 8/1997 | Barbas et al. |
| 5,674,753 | A | 10/1997 | Harvey et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,821,047 | A | 10/1998 | Garrard et al. |
| 5,969,108 | A | 10/1999 | McCafferty et al. |

FOREIGN PATENT DOCUMENTS

| | | |
|---|---|---|
| CA | 2026250 | 3/1991 |
| EP | 0 412 116 B1 | 11/1995 |
| EP | 0 494 135 B1 | 4/1996 |
| WO | WO 86/05807 | 10/1986 |
| WO | WO 89/01036 | 2/1989 |

OTHER PUBLICATIONS

Serum sErbB1 and Epidermal Growth Factor Levels As TumorBiomarkers in Women with Stage III or IV Epithelial Ovarian cancer Andre T. Baron, Jacqueline M. Lafky, et al vol. 8, 129-137, Feb. 1999.*
The detection of increased amounts of the extracellular domain of the epidermal growth factor receptor in serum during carcinogenesis in asbestosis patients. J Occup Med. Dec. 1994;36(12):1324-8. Partanen R, Hemminki K, Koskinen H, Luo JC, Carney WP, Brand.*
Heterodimerization and functional interaction between EGF receptor family members: a new signaling paradigm with implications for breast cancer research. Earp HS, Dawson, et Breast Cancer Res Treat. Jul. 1995;35(1):115-32.*
Prognostic significance of p105 (c-erbB-2 HER2/neu) serum levels in patients with ovarian cancer. Anticancer Res. Jan.-Feb. 1997;17(1B):757-60. Meden H, Marx D, Schauer A, Wuttke W, Kuhn W.*
Her-2/neu and EGFR oncoprotein expression in breast, ovarian and cervical cancers. Carney, WP, Williams Julie, Advance for adinstrators of the laboratory, vol. 10, p. 34, 2001.*
expression of herstatin, an alternative Her-2/NEU product, in cells that express either p185HER-2 or the EGF receptor inhibits receptor activity and cell growth WO02/14470 A2, International Publication date, Feb. 21, 2002.*
Detection of increased amounts of the extracellular domain of the c-erbB-2 oncoprotein in serum during pulmonary carcinogenesis in humans. Int J Cancer. Feb. 1, 1994;56(3):383-6. Brandt-Rauf PW, Luo JC, Carney WP, Smith S, De Vivo I, Milling C, Hemminki K.*

(Continued)

*Primary Examiner*—Larry R. Helms
*Assistant Examiner*—Lei Yao
(74) *Attorney, Agent, or Firm*—Kevin Stein, Esq

(57) ABSTRACT

The present invention describes clinically and medically important methods of monitoring the outcome of a cancer patient who is suffering from disease or who is undergoing treatment or therapy for his or her disease. More specifically, the invention provides a method of monitoring the progression of disease or cancer treatment effectiveness in a cancer patient by measuring the level of the extracellular domain (ECD) of the epidermal growth factor receptor (EGFR) in a sample taken from the cancer patient, preferably, before treatment, at the start of treatment, and at various time intervals during treatment, wherein a decrease in the level of the ECD of the EGFR in the cancer patient compared with the level of the ECD of the EGFR in normal control individuals serves as an indicator of cancer advancement or progression and/or a lack of treatment effectiveness for the patient. As another aspect of determining disease outcome and survival, the invention further provides assessing both EGFR and HER-2/neu levels, in combination, in a patient sample. A finding of decreased levels of EGFR concomitantly with elevated or increased levels of HER-2/neu relative to control levels indicates poor outcome and short time to progression.

9 Claims, 6 Drawing Sheets

OTHER PUBLICATIONS

Hudelist et al., Eur J Cancer, vol. 42, p. 186-92, 2005.*
Jacot et al., Br J Cancer, vol. 91, p. 430-3, 2004.*
Carney et al., Abstract #240, American Association of Cancer Research, Annual Meeting, Apr. 2002.*
Krainer et al., Oncology, vol. 54, p. 475-81, 1997, abstract.*
Payne et al., Clinical Chemistry, vol. 46, p. 175-182, 2000.*
Marx III et al., Abstract #1743, American Society of Clinical oncology, May, 2002.*
Int'l. Search Report, dated Apr. 14, 2005, corresponding to PCT/US03/05831.
Jacot et al. Serum EGF-receptor and HER-2 extracellular and prognosis of non-small-cell lung cancer. British Journal of Cancer. 2004, vol. 91, pp. 430-433.
Partanen et al. The Detection of Increased Amounts of the Extracellular Domain of the Epidermal Growth Factor Receptor in Serum During Carcinogenesis in Asbestosis Patients. Journal of Occupational Medicine. Dec. 1994, vol. 36, No. 12, pp. 1324-1328.
Zhou et al. Clinical Applications of Oncogenes and Oncoproteins: HER-2/neu and EGFR as New Therapeutic Targets. Frontiers of Biotechnology & Pharmaceuticals. 2002, vol. 3, pp. 29-45.
W. J. Gullick et al., *Cancer Res.*, 1986, 46:285-292.
S. Cohen et al, *J. Biol. Chem.*, 1980, 255: 4834-4842.
A.B. Schreiber et al., *J. Biol. Chem.*, 1983, 258:846-853.
Wilson et al., *Cell*, 1984, 37: 767-778.
Francis et al., J. Gen. Virol., 1985, 66: 2347-2354.
Foecking et al., Gene, 1986, 45: 101-105.
Cockett et al., Bio/Technology, July 1990, 8:662-667.
R.N. Fabricant et al., Proc. Natl. Acad. Sci. USA, 1977, 74: 565-569.
M.M. Wrann et al., J. Biol. Chem., 1979, 254: 8083-8086.
S.J. McKenzie et al., Oncogene, 1989, 4: 543-548.
P.K. Smith et al., Analyt. Biochem., 1985, 150: 76-85.
M.M. Bradford, Analyt. Biochem., 1976, 72: 248-254.
O.H. Lowry et al., J. Biol. Chem., 1951, 193: 265-275.
A. Ullrich et al., *Cell*, 1990, 61: 203-212.
R. Nicolson et al., *British Journal Cancer*, 1991, 63: 146-150.
R.G. Dullea, Proc. $91^{st}$ Ann. Meeting of the American Association for Cancer Research (AACR), 2000, 41 (Abstract #2550): 401.
J.M. Nelson et al, Proc. $91^{st}$ Ann. Meeting of the American Association for Cancer Research (AACR), 2000, 41 (Abstract #1533): 241.
T. O'Reilly et al., Proc. $91^{st}$ Ann. Meeting of the American Association for Cancer Research (AACR), 2000, 41 (Abstract #3069): 481.
H.C. Kelly et al., Proc. $91^{st}$ Ann. Meeting of the American Association for Cancer Research (AACR), 2000, 41 (Abstract #3896): 612.
L. Witters et al., *Breast Cancer Research and Treatment*, 1999, 53: 41-50.
X.-D. Yang et al., Proc. $91^{st}$ Ann. Meeting of the American Association for Cancer Research (AACR), 2000, 41 (Abstract #3380): 530.
X.-D. Yang et al., *Cancer Research*, 1999, 59: 1236-1243.
L. Milas et al., *Clinical Cancer Research*, 2000, 6: 701-708.
T. Ohmori et al., Proc. $91^{st}$ Ann. Meeting of the American Association for Cancer Research (AACR), 2000, 41 (Abstract #3072): 482.
A. Budillon et al., Proc. $91^{st}$ Ann. Meeting of the American Association for Cancer Research (AACR), 2000, 41 (Abstract #4910): 773.
W.P. Carney et al., *J. Tumor Marker Oncol.*, 1991, 6(2): 53-72.
A.J. Baron et al., *Cancer Epidemiology, Biomarkers and Prevention*, 1999, 8: 129-137.
Brinkman et al., J. Immunol. Methods, 1995, 182: 41-50.
Ames et al., J. Immunol. Methods, 1995, 184: 177-186.
Kettleborough et al., Eur. J. Immunol., 1994, 24: 952-958.
Persic et al., Gene, 1997, 187: 9-18.
Burton et al., Advances in Immunology, Dixon et al. (eds.), 1994, 57: 191-280.
Kohler et al., Nature, 1975, 256: 495-497.
Harlow et al., Antibodies: A Laboratory Manual, Cold Spring Harbor Laboratory Press, $2^{nd}$ Ed., 1988, p. 1-10.
Hammerling et al., Monoclonal Antibodies and T-Cell Hybridomas, Elsevier, N.Y., 1981, pp. 563-587.
Kozbor et al., Immunol. Today, 1983, 4: 72-79.
Cole et al., Monoclonal Antibodies and Cancer Therapy, Reisfield et al. (eds.), Alan R. Liss, Inc., 1985, pp. 77-96.
Sutcliffe et al., Science, 1983, 219: 660-666.
L. Harris et al., *Int. J. Biol. Markers*, 1999, 14: 8-15.
J. Mendelsohn et al, *Oncogene*, 2000, 19: 6550-6565.
A. L. Ulrich et al., *Nature*, 1984, 307: 418-425.
J. Downward et al., *Nature*, 1984, 307: 521-527.
C.R. Carlin et al., *Mol. Cell. Biol.*, 1986, 6: 257-264.
F.L.V. Mayes et al., *The EMBO J.*, 1984, 3: 531-537.
G. Carpenter et al., *Ann. Rev. Biochem.*, 1979, 48: 193-216.
M.-J. Oh et al., *Clin. Cancer Res.*, 2000, 6: 4760-4763.
W.P. Carney et al, Advance Newsmagazines for Medical Laboratory Professionals, Jun. 2001, 13 (13) : 18.
B. Ozanne et al., *J. Pathol.*, 1986, 149: 9-14.
S.J. McKenzie, *Biochim. et Biophys. Acta*, 1991, 1072: 193-214.
C. Wright et al., *Br. J. Cancer*, 1992, 65: 118-121.
G.N. Fuller et al., *Mutation Res.*, 1992, 276: 299-306.
J.G.M. Klijn et al., *Endocrine Rev.*, 1992, 13: 3-17.
S. Nicolson et al., *Diagnostic Oncology*, 1991, 1: 43-52.
C. Wright et al., *Br. J. Cancer*, 1991, 63: 967-970.
J.-H. Choi et al., Proc. $87^{th}$ Ann. Meeting of the American Association for Cancer Research (AACR), 1996, 37 (Abstract #1413): p. 207.
J.R.C. Sainsbury et al., *Lancet*, 1987, 1: 1398-1402.
M.A. Rios et al., *Anticancer Research*, 1988, 8: 173-176.

* cited by examiner

Serum EGFr

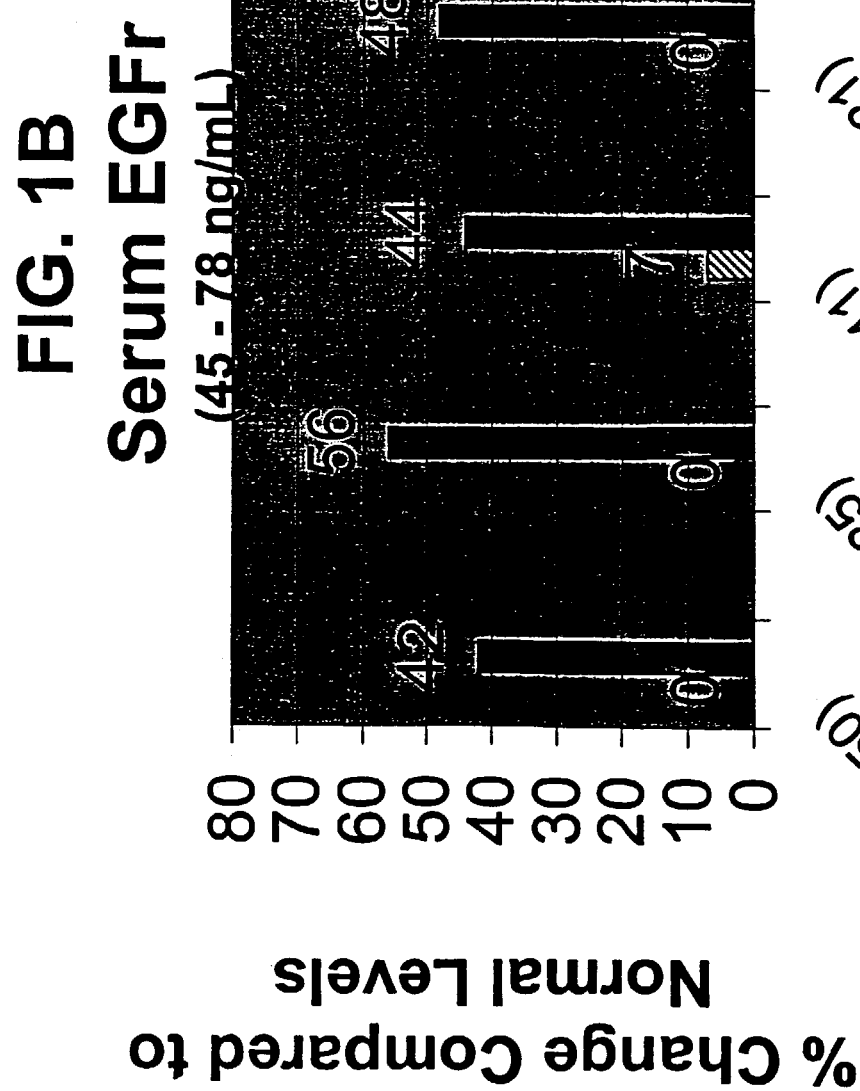
FIG. 1B Serum EGFr (45-78 ng/mL)

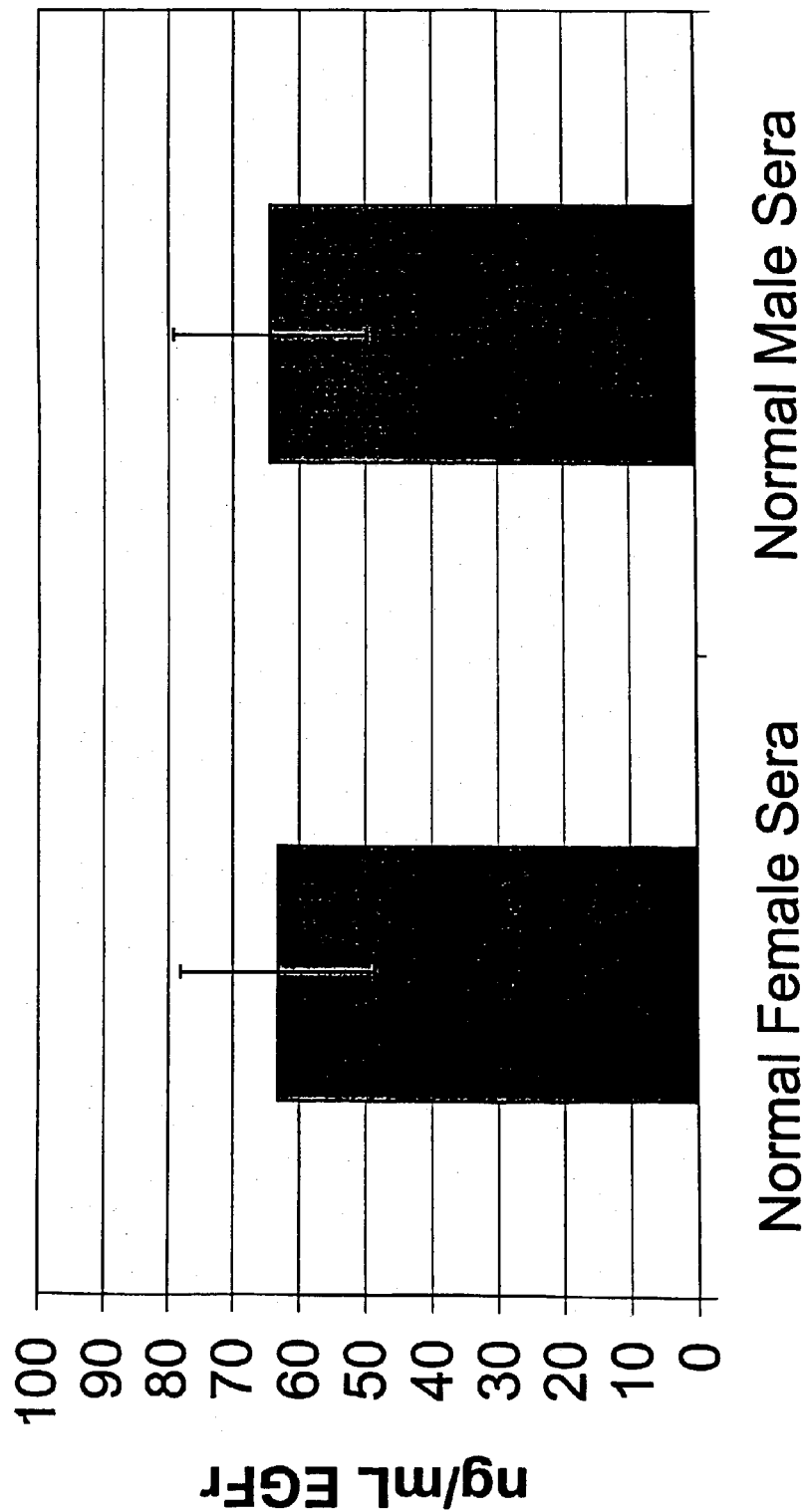

Overall Survival: Interaction of Serum HER-2/neu and EGFR Levels

ASSAYS FOR CANCER PATIENT MONITORING BASED ON LEVELS OF EPIDERMAL GROWTH FACTOR RECEPTOR (EGFR) EXTRACELLULAR DOMAIN (ECD) ANALYTE, ALONE OR IN COMBINATION WITH OTHER ANALYTES, IN BODY FLUID SAMPLES

CROSS-REFERENCE TO RELATED APPLICATIONS

This application claims priority to U.S. Provisional Application No. 60/360,678 filed on Mar. 1, 2002 and U.S. Provisional Application No. 60/429,487 filed on Nov. 27, 2002 under 35 U.S.C. §119(e), the entirety of all of which are incorporated herein by reference as if fully set forth herein.

FIELD OF THE INVENTION

The present invention relates to assays for monitoring or assessing the progress of cancer patients during a course of disease or disease treatment or therapy by determining levels of a cancer analyte, i.e., the extracellular domain, or ectodomain, (ECD), of the epidermal growth factor receptor (EGFR), compared to the levels of the EGFR ECD in normal controls. According to an aspect of the methods described herein, the determination of a decrease in a patient's EGFR ECD levels compared with the levels of this analyte in normal controls is indicative of poor patient and/or treatment outcome relative to disease status. According to another aspect of this invention, the determination of a decrease in a patient's EGFR ECD levels, in combination with the determination of levels of one or more additional analytes, e.g., an increase in HER-2/neu levels, provides further diagnostic and prognostic clinical information related to patient disease progression and overall survival.

BACKGROUND OF THE INVENTION

Epidermal growth factor receptor (EGFR) is a 170 kilodalton (kDa) membrane-bound protein expressed on the surface of epithelial cells. EGFR is a member of the growth factor receptor family of protein tyrosine kinases, a class of cell cycle regulatory molecules. (W. J. Gullick et al., 1986, *Cancer Res.*, 46:285-292). EGFR is activated when its ligand (either EFR or TGFα) binds to the extracellular domain, resulting in autophosphorylation of the receptor's intracellular tyrosine kinase domain (S. Cohen et al., 1980, *J. Biol. Chem.*, 255:4834-4842; A. B. Schreiber et al., 1983, *J. Biol. Chem.*, 258:846-853).

EGFR is the protein product of a growth promoting oncogene, erbB or ErbB1, that is but one member of a family, i.e., the ERBB family of protooncogenes, believed to play pivotal roles in the development and progression of many human cancers. The ERBB family of oncogenes encodes four, structurally-related transmembrane receptors, namely, EGFR, HER-2/neu (erbB2), HER-3 (erbB3) and HER-4 (erbB4). Clinically, ERBB oncogene amplification and/or receptor overexpression in tumors have been reported to correlate with disease recurrence and poor patient prognosis, as well as with responsiveness in therapy. (L. Harris et al., 1999, *Int. J. Biol. Markers*, 14:8-15; and J. Mendelsohn and J. Baselga, 2000, *Oncogene*, 19:6550-6565).

EGFR is composed of three principal domains, namely, the extracellular domain (ECD), which is glycosylated and contains the ligand-binding pocket with two cysteine-rich regions; a short transmembrane domain, and an intracellular domain that has intrinsic tyrosine kinase activity. The transmembrane region joins the ligand-binding domain to the intracellular domain. Amino acid and DNA sequence analysis, as well as studies of nonglycosylated forms of EGFR, indicate that the protein backbone of EGFR has a mass of 132 kDa, with 1186 amino acid residues (A. L. Ullrich et al., 1984, *Nature*, 307:418-425; J. Downward et al., 1984, *Nature*, 307: 521-527; C. R. Carlin et al., 1986, *Mol. Cell. Biol.*, 6:257-264; and F. L. V. Mayes and M. D. Waterfield, 1984, *The EMBO J.*, 3:531-537).

The binding of EGF or TGFα to EGFR activates a signal transduction pathway and results in cell proliferation. The dimerization, conformational changes and internalization of EGFR molecules function to transmit intracellular signals leading to cell growth regulation (G. Carpenter and S. Cohen, 1979, *Ann. Rev. Biochem.*, 48:193-216). Genetic alterations that affect the regulation of growth factor receptor function, or lead to overexpression of receptor and/or ligand, result in cell proliferation. In addition, EGFR has been determined to play a role in cell differentiation, enhancement of cell motility, protein secretion, neovascularization, invasion, metastasis and resistance of cancer cells to chemotherapeutic agents and radiation. (M.-J. Oh et al., 2000, *Clin. Cancer Res.*, 6:4760-4763).

Cancer results from a series of genetic alterations which can include activation of oncogenes that promote cell growth and/or the loss of tumor suppressor gene function, which inhibits cell growth. While mutation or overexpression of oncogenes produces proteins that can stimulate uncontrolled cell growth, mutation or deletion of tumor suppressor genes results in the production of non-functional proteins that no longer control cell proliferation. (W. P. Carney and J. Williams, 2001, AdvanceLaboratory, *Women's Health*, pp.1-3).

A number of reports have indicated that the overexpression of EGFR occurs in many tumors, cancers, and malignancies; specifically, in breast, squamous cell, head and neck, glioma, lung, gastric, pancreatic, bladder, cervix, ovarian and prostate cancers. (M.-J. Oh et al., 2000, Ibid.; (W. J. Gullick et al., 1986, *Cancer Res.*, 46:285-292; B. Ozanne et al., 1986, *J. Pathol.*, 149:9-14; S. J. McKenzie, 1991, *Biochim. et Biophys. Acta*, 1072:193-214; C. Wright et al., 1992, *Br. J. Cancer*, 65:118-212; G. N. Fuller et al., 1992, *Mutation Res.*, 276:299-306; J. G. M. Klijn et al., 1992, *Endocrine Rev.*, 13:3-17; S. Nicolson et al., 1991, *Oncology*, 1:43-52; and C. Wright et al., 1991, *Br. J. Cancer*, 63:967-970). The exact role of EGFR in tumorigenesis remains to be determined; however, some studies of breast cancer patients have suggested that elevated EGFR in tumors may correlate with poor prognosis and disease progression parameters, such as invasion or lymph node metastasis (J.-H. Choi et al., 1997, $87^{th}$ *Ann. Meeting AACR*, Washington, D.C., Apr. 20-24, 1996, pp. 1879-1883; J. G. M. Klijn et al., 1992, *Endocrine Reviews*, 13:3-17; S. Nicolson et al., 1991, *Diagnostic Oncology;* 1:43-52; C. Wright et al., 1991, *British Journal Cancer*, 63:967-970; J. R. C. Sainsbury et al., 1987, *Lancet*, 1:1398-1402; M. A. Rios et al., 1988, *Anticancer Research*, 8:173-176; A. Ullrich et al., 1990, *Cell*, 61:203-212; R. Nicolson et al., 1991, *British Journal Cancer*, 63:146-150).

Recent work has shown that tumors that overexpress EGFR may be amenable to treatment with a variety of therapies that target EGFR. Such treatments include small molecule inhibitors of the kinase activity of EGFR (R. G. Dullea et al., 2000, *Proc. $91^{st}$ Ann. Meeting of the American Association for Cancer Research (AACR)*, 41 (Abstract #2550): 401; J. M. Nelson et al., 2000, *Proc. $91^{st}$ Ann. Meeting AACR*, 41 (Abstract #2533):241; T. O'Reilly et al., 2000, *Proc. $91^{st}$ Ann. Meeting AACR*, 41 (Abstract #3069):481; and H. C.

Kelly et al., 2000, *Proc. 91st Ann. Meeting AACR*, 41 (Abstract #3896):612); antisense oligonucleotides (L. Witters et al., 1999, *Breast Cancer Research and Treatment*, 53:41-50); and immunotherapies that act directly on EGFR (X-D Yang et al., 2000, *Proc. 91st Ann. Meeting AACR*, 41 (Abstract #3380):530; X-D Yang et al., 1999, *Cancer Research*, 59:1236-1243; and L. Milas et al., 2000, *Clinical Cancer Research*, 6:701-708). Such therapies can be combined with traditional chemotherapy regimens in order to increase therapeutic efficacy in a variety of cancers (T. Ohmori et al., 2000, *Proc. 91st Ann. Meeting AACR*, 41 (Abstract #3072):48236 and A. Budillon et al., 2000, *Proceedings of the 91st Ann. Meeting AACR*, 41 (Abstract #4910):773).

In addition to EGFR, Human Epidermal Growth Factor Receptor-2 (also termed HER-2, HER-2/neu, neu, or c-erbB-2), another cell surface growth factor receptor of the ERBB family of receptor tyrosine kinases, has also been reported to be associated with uncontrolled cell proliferation and cancers. Like EGFR, HER-2/neu is a transmembrane tyrosine kinase receptor expressed on epithelial cells. The full-length HER-2/neu polypeptide has a molecular weight of 185 kDa (p185).

The ECDs of both EGFR and HER-2/neu have been shown to be released from the cell surface and have been found to circulate in normal people and in cancer patients. The ECD or shed ECD of HER-2/neu is a glycoprotein of between 97 and 115 kDa, referred to as p105 (W. P. Carney et al., 1991, *J. Tumor Marker Oncol.*, 6(2):53-72). The primary ECD of EGFR is 110 kDa and is referred to as p110. Smaller circulating fragments of EGFR have also been reported. (A. J. Baron et al., 1999, *Cancer Epidemiology, Biomarkers and Prevention*, 8:129-137). patients. The shed ECD of HER-2/neu has been shown to be elevated in cancer patient serum (e.g., W. P. Carney et al., 1991, *J. Tumor Marker Oncol.*, 6(2):53-72). Elevations in EGFR have mainly been documented at the tissue level, based on the analysis of the full length EGFR, p170. Increased EGFR ECD levels have been reported in the sera of cervical cancer patients. (M.-J. Oh et al., 2000, *Clin. Cancer Res.*, 6:4760-4763).

Because both EGFR and HER-2/neu are expressed in at least 20-40% of women with breast, ovarian and cervical cancers, as well as in a wide variety of other cancers affecting both genders, it is a problem in the art to be able to accurately and sensitively identify, screen and monitor those individuals who are likely to respond, and who are responding to, or benefiting from, anti-EGFR therapy and/or anti-HER-2/neu therapy, conventional anti-cancer or anti-neoplastic treatments or therapies, or combination therapies, where applicable.

The present invention solves such a problem by providing a sensitive and reliable method, particularly an immunoassay method, to determine changed levels, particularly, decreased levels, of EGFR ECD in body fluid samples of cancer patients relative to those of normal individuals. Methods are also provided in which levels of EGFR ECD are determined in conjunction with the levels of other analytes, in particular, HER-2/neu, to diagnose and/or prognose disease progression and survival in cancer patients. In addition, the present invention is advantageous in that it is employed to monitor cancer patients undergoing cancer or anti-neoplastic treatments and therapies for cancers associated with overexpression of EGFR to assist in the determination of cancer treatment progress and patient outcome during the course of disease and/or anti-cancer therapy(ies).

SUMMARY OF THE INVENTION

The present invention provides an assay (method) for the analysis of body fluid samples, particularly, serum or plasma samples, in cancer patients to detect and measure changes in the levels of the ECD shed from the EGFR, as well as ECD that is actively cleaved from the EGFR, and particularly, to determine whether there is a decrease in such ECD EGFR levels in cancer patients compared to the ECD EGFR levels found in normal individuals.

In accordance with this invention, the determination of a measurable decrease in EGFR ECD levels in the cancer patient's body fluid sample compared with the EGFR ECD levels in normal controls is an indication of disease severity, poor patient response to treatment, and/or poor patient outcome from disease. Thus, knowledge of patient progress and/or treatment efficacy, or lack thereof, is provided by the practice of the method of this invention. This information is available to the medical community, the physician and the patient to assist in making informed decisions concerning a patient's cancer treatment and the consequences of treatment and disease during the course of the disease and/or treatment or therapy for the disease.

A particular aspect of the present invention provides a monitoring method in which serum levels of the ECD of EGFR in breast cancer patients are monitored during the course of cancer or anti-neoplastic treatment, and also preferably, prior to and at the start of treatment. The determination of a decrease in the serum levels of EGFR ECD in the breast cancer patient compared to the levels of EGFR ECD in normal individuals without cancer allows the following evaluation related to patient progression and/or outcome: (i) a more severe stage or grade of the cancer; (ii) shorter time to disease progression, and/or (iii) lack of a positive, i.e., effective, response by the patient to the cancer treatment.

Another aspect of the present invention provides a monitoring method in which levels of the EGFR ECD in a body fluid sample of patients having a cancer or neoplastic disease, for example, of the colon, bladder, prostate, breast (mammary), or lung, are monitored during the course of cancer or anti-neoplastic treatment, and preferably prior to, or just at, the start of treatment. The determination of a decrease in the sample levels of the EGFR ECD analyte in the cancer patient compared to the normal levels of EGFR ECD allows the practitioner to be able to evaluate the patient's disease progression and/or outcome of disease. For example, based on the monitoring of a patient's EGFR ECD analyte levels over time relative to normal levels of this analyte, as well as to the patient's own prior-determined levels, a determination can be made as to whether a treatment regimen should be changed, i.e., to be more aggressive or less aggressive; to determine if the patient is responding favorably to his or her treatment; and/or to determine disease status, such as advanced stage or phase of the cancer, or a remission, reduction or regression of the cancer or neoplastic disease.

A further aspect of the present invention provides in vitro assays for cancer patient monitoring to assess the course of a cancer patient's disease and/or patient response to cancer treatment or therapy using body fluid samples to measure and determine a decrease in the levels of EGFR ECD in the body fluid sample compared with a normal range level of EGFR ECD in healthy individuals as controls. In accordance with particular embodiments, the monitoring involves patients having metastatic breast cancer, or other types of cancers, whereby the severity of the grade or stage of the cancer is correlated with the percent decrease in EGFR ECD levels in the patient's sample compared with the EGFR ECD levels in normal controls.

Yet another aspect of this invention provides a normal range of EGFR ECD in the sera of healthy male and female individuals for use in comparing the EGFR ECD levels in the sera of patients undergoing testing according to the present methods.

Another aspect of the present invention provides assays and methods for cancer patient testing and monitoring, particularly breast cancer patient, and more particularly, metastatic breast cancer patient testing and monitoring, to assess the course and outcome of the cancer patient's disease, and/or patient response to cancer treatment or therapy. The assays and methods employ body fluid samples to measure and determine a decrease in the levels of EGFR ECD in combination with an increase in the levels of HER-2/neu (>15 ng/ml), preferably HER-2/neu ECD, in the body fluid sample compared with the normal range levels of EGFR ECD and HER-2/neu in normal individuals as controls. The analysis of EGFR and HER-2/neu levels, in combination, provides new medical and clinical insight about a cancer patient's response, treatment, prognosis, course of disease and survival outcome that can enhance diagnostic and prognostic assessments of the patient.

In accordance with a related particular embodiment, the assay and method involve patients having breast cancer, especially metastatic breast cancer, in which the finding of a combination of elevated serum HER-2/neu levels, preferably, HER-2/neu ECD levels, and decreased EGFR ECD levels in the patient's sample was indicative of a shorter time to progression and shorter overall survival time compared with women having breast cancer who had one or more of the following characteristics: a) normal EGFR levels (e.g., 45-78 ng/ml) and normal HER-2/neu ECD levels (e.g., <15 ng/ml); b) normal EGFR levels and elevated HER-2/neu levels (e.g., ≧15 ng/ml); and/or c) decreased EGFR levels, but normal HER-2/neu levels. This aspect of the present invention is particularly advantageous, as it allows the physician to more effectively select the best treatments, as well as to utilize more aggressive treatments and therapy regimens, for women whose levels of the EGFR oncoprotein is reduced and whose levels of the HER-2/neu oncoprotein is elevated to counteract their poor prognosis and overall survival time relative to control individuals.

Another aspect of this invention provides a normal value for HER-2/neu levels in an individual's serum sample, preferably, a female individual, for use in comparing the HER-2/neu ECD levels in the sera of patients undergoing testing according to the present methods. In accordance with these methods, a normal HER-2/neu level is defined as less than 15 ng/ml, while an elevated level is defined as greater than or equal to 15 ng/ml.

Further aspects, features and advantages of the present invention will be better appreciated upon a reading of the detailed description of the invention when considered in connection with the accompanying figures/drawings.

BRIEF DESCRIPTION OF THE FIGURES

FIGS. 1A and 1B illustrate the change in serum EGFR ECD levels compared to the levels of serum EGFR ECD in normal individuals as determined following the practice of the method according to the present invention employing samples from cancer patients having cancer of the lung, bladder, prostate, ovary, breast and colon. FIG. 1A shows the change in EGFR ECD in the sera of cancer patients as an increase or decrease compared to the EGFR ECD levels in normal controls. FIG. 1B presents the percent change in serum EGFR ECD levels of cancer patients compared to normal serum levels of EGFR ECD, where the normal range for EGFR ECD is 45-78 ng/ml. For lung cancer patients' EGFR ECD levels, the percent increase was 0%, and the percent decrease was 42%; for bladder cancer patients' EGFR ECD levels, the percent increase was 0%, and the percent decrease was 56%; for prostate cancer patients' EGFR ECD levels, the percent increase was 7%, and the percent decrease was 44%; for ovarian cancer patients' EGFR ECD levels, the percent increase was 0%, and the percent decrease was 48%; for breast cancer patients' EGFR ECD levels (stage IV breast cancer), the percent increase was 2%, and the percent decrease was 32%; and for colon cancer patients' EGFR ECD levels, the percent increase was 0%, and the percent decrease was 67%.

FIG. 2 illustrates the mean serum EGFR ECD values (in ng/ml) as determined in normal male sera and in normal female sera. (Table 1).

FIG. 4 illustrates the probability of progression from the start of cancer therapy versus time (days) based upon the analysis of pretreatment serum samples from 265 women having breast cancer, in which the following combinations of oncoprotein analyte levels were determined and compared:

a) normal EGFR levels/normal HER-2/neu levels (<15 ng/ml);

b) low EGFR levels/normal HER-2/neu levels (<15 ng/ml);

c) elevated HER-2/neu levels (≧15 ng/ml)/normal EGFR levels; and d) elevated HER-2/neu levels (≧15 ng/ml)/low EGFR levels.

For a) versus b) above, p=0.45; for c) versus d) above, p=0.01. As can be observed from the results, the time to progression is determined to be about 6 months for those patients having elevated HER-2/neu serum levels combined with low EGFR serum levels, versus (i) over about 1.5 years for patients having elevated HER-2/neu levels combined with normal EGFR levels, or low EGFR levels combined with normal HER-2/neu levels; and (ii) over about 3.5 years for patients having normal EGFR levels and normal HER-2/neu levels.

Figure 5:
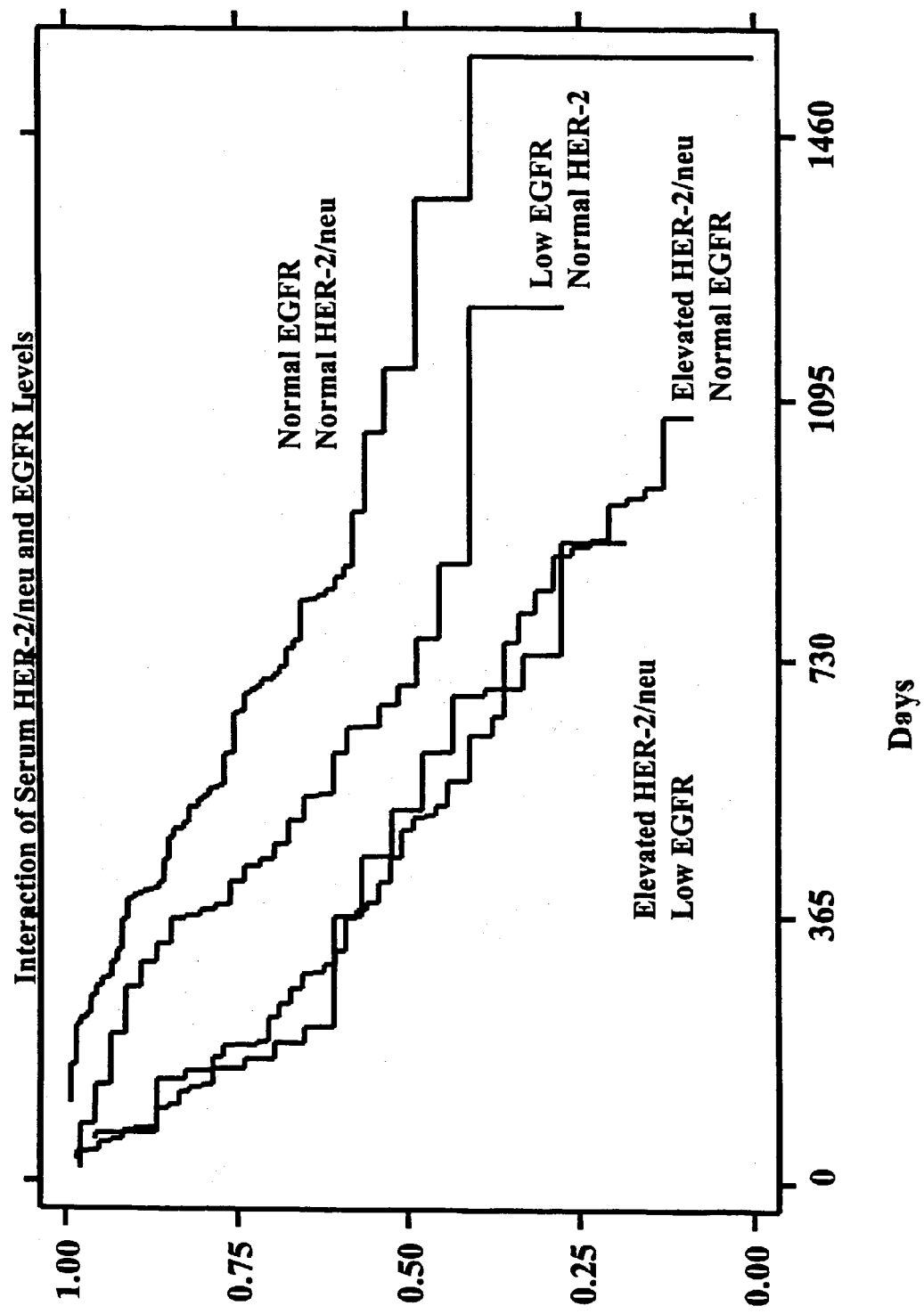

FIG. 5 depicts the overall survival time for breast cancer patients, based upon an assessment of the combination of serum EGFR and HER-2/neu levels in the sera of women with breast cancer. FIG. 5 illustrates the probability of survival from the start of cancer therapy versus time (days) based upon the analysis of serum samples (n=23) from women having breast cancer, in which the following combinations of oncoprotein analyte levels were determined and compared:

a) normal EGFR levels/normal HER-2/neu levels (<15 ng/ml);

b) low EGFR levels/normal HER-2/neu levels (<15 ng/ml);

c) elevated HER-2/neu levels (≧15 ng/ml)/normal EGFR levels; and d) elevated HER-2/neu levels (≧15 ng/ml)/low EGFR levels.

For a) versus b) above, p=0.06; for b) versus d), p=0.03; and for c) versus d), p=0.18. As can be observed from the results, the overall survival time is about 2.5 years for those patients having elevated HER-2/neu serum levels combined with low EGFR serum levels. The overall survival time for patients having elevated HER-2/neu levels combined with normal EGFR levels is slightly less than about 3 years. For those patients having low EGFR levels combined with normal HER-2/neu levels, the overall survival time is nearly 3.5 years, while the overall survival time for patients having normal EGFR levels and normal HER-2/neu levels is over 4 years.

DETAILED DESCRIPTION OF THE INVENTION

The present invention relates to an accurate and sensitive determination of whether cancer patients have decreased levels of the extracellular domain or ectodomain (ECD) of EGFR relative or compared to the levels of this analyte in normal individuals. The determination of lower or decreased levels of the EGFR ECD analyte in a body fluid sample of a cancer patient comprises a method or assay especially for use to screen over time, or monitor, cancer patients undergoing cancer therapies, including anti-EGFR therapies, such as those described herein, to assess one or more of the following parameters: therapeutic efficacy, patient response, patient status, progress of therapy and the clinical course and/or outcome of the cancer or neoplastic disease. The present methods also encompass a method of determining or assessing patient outcome or disease severity, based on the determination of decreased levels of the EGFR ECD analyte in cancer patients compared to the levels of these analytes in normal individuals.

The present invention encompasses the use of the described in vitro analysis methods to assess patients having a variety of types of cancers, tumors, or neoplasms. Non-limiting examples of cancers, tumors, and neoplastic diseases embraced by this invention include solid tumor cancers, and cancers of the lung; breast (mammary); prostate; gynecological cancers, such as those of the cervix, ovary, vulva, vagina and endometrium; urinary tract cancers, such as those of the bladder; cancers of the pancreas; esophagus; head and neck; kidney; liver; stomach (gastric); and colon.

This invention further embodies the ability to monitor or examine the progression of a given cancer over the course of analysis or treatment as described herein. For example, the performance of the method of this invention provides a determination of a correlation between decreased EGFR ECD levels compared to normal EGFR ECD levels (i.e., a comparison with a normal range, a normal value, or a normal cutoff value), and stage or grade of a cancer, such as breast cancer, ovarian cancer, and prostate cancer. In, addition, for metastatic breast cancer, the invention allows a determination of clinical benefit, time to progression (TTP), and length of survival time based upon the findings of decreased levels of EGFR ECD compared to the levels of this analyte in normal individuals, preferably in serum samples.

In accordance with this invention, the analysis preferably involves a body fluid sample, or a tissue sample, taken from a mammal, preferably a human, more preferably a cancer patient. It is to be understood that body fluid or tissue samples from other mammals, e.g., non-human primates, and other large and small animals, are able to be monitored by the methods as described herein. Suitable body fluids include, but are not limited to, pleural fluid samples, pulmonary or bronchial lavage fluid samples, synovial fluid samples, peritoneal fluid samples, bone marrow aspirate samples, lymph, cerebrospinal fluid, ascites fluid samples, amniotic fluid samples, sputum samples, bladder washes, semen, urine, saliva, tears, blood, and its components serum and plasma, and the like. Serum is a preferred body fluid sample, as it allows for real-time assessment of the EGFR status of a cancer patient, allows for repeated testing for patient monitoring and can be performed in a standardized and quantitative manner. Suitable tissue samples include various types of tumor or cancer tissue, or organ tissue, such as those taken at biopsy.

In another of its embodiments, the present invention encompasses assays and methods for cancer patient testing and monitoring, particularly breast cancer patient testing and monitoring, and more particularly, metastatic breast cancer testing and monitoring, to assess the course and outcome of the cancer patient's disease, and/or patient response to cancer treatment or therapy by measuring two analytes in combination. More specifically, the assays and methods employ a patient's body fluid sample to measure and determine, in combination, a decrease in the levels of EGFR ECD and an increase in the levels of HER-2/neu, preferably, HER-2/neu ECD, in the body fluid sample compared with the normal level values of EGFR and HER-2/neu ECD in individuals used as controls.

The interactions between members of the EGFR superfamily provide a basis for the assessment of the levels of two of receptor proteins in combination in accordance with the present invention. Currently, the EGFR superfamily includes four members, namely, EGFR, HER-2/neu, HER-3 and HER-4. For their activation, these proteins combine to form a complex of two receptors. For example, the complexes can be either homodimers (e.g., HER-2/neu and HER-2/neu; EGFR and EGFR) or heterodimers (e.g., EGFR and HER-2/neu). Newly provided by the present invention is a diagnostic and prognostic tool for determining clinical outcome comprising an evaluation of HER-2/neu and EGFR levels, in combination, to assist the medical practitioner and the patient in targeting certain therapies for patient treatment, and for selecting the types of treatments that should be used. The invention further provides measurable parameters on which the clinician can rely in determining whether to embark on, continue, or modify a course of treatment and therapy for a patient.

In accordance with a related particular embodiment, the present invention encompasses an assay and method involving patients having cancer, particularly breast cancer, more particularly metastatic breast cancer, in which the finding of a combination of elevated serum HER-2/neu levels (e.g., greater than the normal level of <15 ng/ml) and decreased EGFR ECD levels (e.g., less than the normal range of 45-78 ng/ml) in the patient's sample was indicative of a shorter time to progression and shorter overall survival time compared with women having breast cancer who had one or more of the following characteristics:

a) normal EGFR levels (e.g., 45-78 ng/ml) and normal HER-2/neu ECD levels (e.g., <15 ng/ml);
b) normal EGFR levels and elevated HER-2/neu levels ($\geq 15$ ng/ml); and/or
c) decreased EGFR levels, but normal HER-2/neu levels.

The embodiment encompassing the combined analysis of both EGFR and HER-2/neu ECD levels in patients is particularly valuable and informative, as it allows the physician to more effectively select the best treatments, as well as to utilize more aggressive treatments and therapy regimens, for women whose levels of the EGFR oncoprotein is reduced and whose levels of the HER-2/neu oncoprotein is elevated relative to control individuals. More aggressive treatment, or combination treatments and regimens, can serve to counteract poor patient prognosis and overall survival time. As described in Example 5, patients having elevated serum HER-2/neu and low serum EGFR levels could benefit from combined EGFR- and HER-2/neu-directed therapies, while patients having normal HER-2/neu serum levels and low EGFR levels could benefit from EGFR-directed therapy alone.

In addition, the methods of this invention are beneficial in that they can assist clinicians, medical personnel and practitioners in subdividing breast cancer patients into high risk and low risk populations. Those patients who have EGFR levels below the cutoff normal range of about 45-78 ng/ml and HER-2/neu levels above <15 ng/ml can be determined to be the patients with the shortest time to progression and the shortest overall survival. Armed with this information, the medical practitioner can choose to provide certain types of treatment and/or more aggressive therapy and/or treatment to the patient who is in a high risk category.

In a further embodiment, a normal range of HER-2/neu levels in the sera of individuals, preferably females, is afforded by this invention for use in comparing the HER-2/neu ECD levels in the sera of patients undergoing testing, diagnosis, and/or monitoring according to the present methods. The normal range of HER-2/neu in sera is less than about 15 ng/ml (<15 ng/ml).

In a most preferred embodiment, this invention relates to the testing and analysis of serum levels of EGFR and HER-2/neu oncoproteins in women with metastatic breast cancer to obtain clinically useful information based upon the levels of these oncoproteins, when examined in conjunction with one another. A finding of decreased EGFR levels, wherein decreased refers to levels that are less than the control range of about 45-78 ng/ml, combined with elevated HER-2/neu levels, wherein elevated refers to levels that are greater than the control value of about <15 ng/ml, alerts the clinician that these patients have a shorter time to progression of their cancer, and/or a shorter overall survival time. The values obtained from the patients' samples were compared (i) with values from women having both normal EGFR (45-78 ng/ml) and normal HER-2/neu (<15 ng/ml) levels; (ii) with values from women having normal EGFR levels, but elevated HER-2/neu levels; and (iii) with values from women having decreased EGFR levels, but normal HER-2/neu levels.

According to this invention, the ECD from EGFR can be measured in the body fluid sample, e.g., serum or plasma, using assays that detect the extracellular domain of EGFR, for example, radioisotopic immunoassays or non-isotopic immunoassays, e.g., fluorescent immunoassays, enzymatic immunoassays, such as an enzyme linked immunoassay (ELISA), as are commercially available, known and practiced in the art. (See, e.g., U.S. Pat. Nos. 5,344,760 and 5,674,753 to J. Harvey et al.; EGF-R ELISA (CN Biosciences, Boston, Mass.); and EGFr Microtiter ELISA (Bayer Diagnostics/Oncogene Science, Cambridge, Mass.).

In addition, HER-2/neu (or HER-2/neu ECD) can be measured in the body fluid sample, e.g., serum or plasma, using assays that detect HER-2/neu, and/or the extracellular domain of HER-2/neu, for example, radioisotopic immunoassays or non-isotopic immunoassays, e.g., fluorescent immunoassays, enzymatic immunoassays, such as an enzyme linked immunoassay (ELISA), as are commercially available, known and practiced in the art. (See, e.g., U.S. Pat. No. 5,401,638 and EP 0494135 relating to detection of the p105 domain of HER-2/neu, and U.S. Pat. No. 5,604,107, EP 0412116 and Canadian patent 2,026,250-8 relating to the detection and quantification of the full length p185 protein; HER-2/neu ELISA (CN Biosciences, Boston, Mass.); and HER-2/neu Microtiter ELISA (Bayer Diagnostics/Oncogene Science, Cambridge, Mass.).

By way of example, other means for determining and measuring EGFR ECD levels, as well as HER-2/neu levels, in a sample include affinity chromatography, ligand binding assays and lectin binding assays. Immunoassays, especially non-radioisotopic immunoassays, are preferred. Normal range and normal mean values can be determined for the assay being carried out based on normal (healthy) population samples, as is known and practiced in the art.

Antibodies directed against the EGFR protein, the HER-2/neu protein, or antigenic or immunogenic epitopes thereof, particularly the ECDs of these receptor proteins, can be, for example, polyclonal or monoclonal antibodies. Antibodies suitable for use in the assays of this invention also include chimeric, single chain, and humanized antibodies, as well as Fab, F(ab')$_2$, or Fv fragments, or the product of a phage display library, e.g., an Fab expression library. Various procedures known in the art may be used for the production of such antibodies and antibody fragments. Examples of phage display methods that can be used to make antibodies for use in the present invention include those disclosed in Brinkman et al., 1995, *J. Immunol. Methods,* 182:41-50; Ames et al., 1995, *J. Immunol. Methods,* 184:177-186; Kettleborough et al., 1994, *Eur. J. Immunol.,* 24:952-958; Persic et al., 1997, *Gene,* 187:9-18; Burton et al., 1994, *Advances in Immunology,* 57:191-280; and in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Antibodies generated against the EGFR ECD, the HER-2/neu ECD, or the complete proteins, can be obtained by direct injection of an immunogenic EGFR or HER-2/neu preparation into an animal, or by administering all, or the ECD portion, of the EGFR or the HER-2/neu polypeptides to an animal, preferably a nonhuman animal. For the preparation of monoclonal antibodies, any technique which provides antibodies produced by continuous cell line cultures can be used. Examples include the hybridoma technique (Kohler and Milstein, 1975, *Nature,* 256:495-497; Harlow et al., Antibodies: A Laboratory Manual, (Cold Spring Harbor Laboratory Press, 2nd Ed. 1988; and Hammerling, et al., In: Monoclonal Antibodies and T-Cell Hybridomas, Elsevier, N.Y., pages 563-681, 1981), the trioma technique, the human B-cell hybridoma technique (Kozbor et al., 1983, *Immunol. Today,* 4:72), and the EBV-hybridoma technique to produce human monoclonal antibodies (Cole et al., 1985. In: *Monoclonal Antibodies and Cancer Therapy,* Alan R. Liss, Inc., pp. 77-96). Techniques described for the production of single chain antibodies (U.S. Pat. No. 4,946,778) can be adapted to produce single chain antibodies to the EGFR ECD. Also, transgenic mice may be used to express humanized antibodies to immunogenic EGFR ECD, or the HER-2/neu ECD.

Methods for producing and screening for anti-EGFR ECD-specific antibodies or anti-HER-2/neu ECD-specific antibodies using hybridoma technology are routine and well known in the art. In a nonlimiting example, mice can be immunized with an immunogen, i.e., EGFR ECD polypeptide or peptide thereof, HER-2/neu ECD polypeptide or peptide thereof, or with a cell expressing these polypeptides or peptides. Once an immune response is detected, e.g., antibodies specific for the antigen are detected in the sera of immunized mice, the spleen is harvested and splenocytes are isolated. The splenocytes are then fused by well known techniques to any suitable myeloma cells, for example cells from cell line SP2/0 or P3X63-AG8.653 available from the ATCC. Hybridomas are selected and cloned by limiting dilution techniques. The hybridoma clones are then assayed by methods known in the art to determine and select those cells that secrete antibodies capable of binding to a polypeptide of the invention. Ascites fluid, which generally contains high levels of antibodies, can be generated by injecting mice with positive hybridoma clones.

EGFR polypeptides or HER-2/neu polypeptides comprising one or more immunogenic ECD epitopes which elicit an antibody response can be introduced together with a carrier protein, such as an albumin, to a host animal (such as rabbit, mouse, rat, sheep, or goat). Alternatively, if the polypeptide is of sufficient length (e.g., at least about 25 amino acids), the polypeptide can be presented without a carrier. However, immunogenic epitopes comprising as few as 5 to 10 amino acids have been shown to be sufficient to raise antibodies capable of binding to, at the very least, linear epitopes in a denatured polypeptide (e.g., in Western blotting).

ECD epitope-bearing EGFR protein or HER-2/neu protein or peptides thereof, can be used to induce antibodies according to methods well known in the art including, but not limited to, in vivo immunization, in vitro immunization, and phage display methods. See, e.g., Sutcliffe et al., 1983, *Science*, 219:660-666; Wilson et al., 1984, *Cell*, 37:767-778; and Bittle et al., 1985, *J. Gen. Virol.*, 66:2347-2354). If in vivo immunization is used, animals can be immunized with free peptide; however, the anti-peptide antibody titer may be boosted by coupling the peptide to a macromolecular carrier, such as keyhole limpet hemacyanin (KLH), or tetanus toxoid (TT). For instance, peptides containing cysteine residues can be coupled to a carrier using a linker such as maleimidobenzoyl-N-hydroxysuccinimide ester (MBS), while other peptides may be coupled to carriers using a more general linking agent, such as glutaraldehyde.

Antibodies specific for the ECD of EGFR or of HER-2/neu can be produced by any method known in the art for the synthesis of antibodies, in particular, by chemical synthesis, by intracellular immunization (i.e., intrabody technology), or by recombinant expression techniques. Methods of producing antibodies include, but are not limited to, hybridoma technology, EBV transformation, as well as through the use recombinant DNA technology. Recombinant expression of an antibody, or a fragment, derivative, variant or analog thereof, (e.g., a heavy or light chain of an anti-EGFR ECD antibody, or of an anti-HER-2/neu ECD antibody), requires construction of an expression vector containing a polynucleotide that encodes the antibody. Once a polynucleotide encoding an antibody molecule or a heavy or light chain of an antibody, or portion thereof (preferably containing the heavy or light chain variable domain) has been obtained, the vector for the production of the antibody molecule can be produced by recombinant DNA technology using techniques well known in the art. In vitro recombinant DNA techniques, synthetic techniques, and in vivo genetic recombination methods, which are well known to those skilled in the art, can be used to construct expression vectors containing antibody coding sequences and appropriate transcriptional and translational control signals. Such vectors can include the nucleotide sequence encoding the constant region of the antibody molecule (see, e.g., PCT Publication WO 86/05807; PCT Publication WO 89/01036; and U.S. Pat. No. 5,122,464) and the variable region of the antibody cloned into such a vector for expression of the entire heavy or light chain.

The expression vector is then introduced into a host cell by conventional techniques and the transfected cells are cultured by conventional techniques to produce an anti-EGFR-ECD antibody or an anti-HER-2/neu ECD antibody. A variety of host expression vector systems can be utilized to express the antibody molecules. Such expression systems represent vehicles by which the coding sequences of interest can be expressed, their encoded products produced and subsequently purified. These systems also represent cells which can, when transformed or transfected with the appropriate nucleotide coding sequences, express an antibody molecule of the invention in situ. Cell expression systems include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces or Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus (CaMV) or tobacco mosaic virus (TMV)), transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *E. coli*, and more preferably, eukaryotic cells, especially for the expression of whole recombinant antibody molecules, are used for the expression of a recombinant antibody molecule. For example, mammalian cells such as Chinese hamster ovary (CHO) cells, in conjunction with a vector such as the major intermediate early gene promoter element from human cytomegalovirus, is an effective expression system for antibody production (Foecking et al., 1986, *Gene*, 45:101; Cockett et al., 1990, *BioTechnology*, 8:2).

Once an anti-EGFR ECD or an anti-HER-2/neu antibody has been produced by an animal, chemically synthesized, or recombinantly expressed, it can be purified by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins.

Typically, an ELISA assay initially involves preparing an antibody specific to the EGFR or the HER-2/neu ECD, preferably a monoclonal antibody. In addition, a reporter antibody is used. In some ELISA protocols, the reporter antibody recognizes and binds to the anti-EGFR ECD-specific monoclonal antibody, or to the anti-HER-2/neu ECD-specific monoclonal antibody. To the reporter antibody is attached a detectable reagent such as a radioactive isotope, a fluorescent moiety, a chemiluminescent moiety, or, in an ELISA, an enzyme, such as horseradish peroxidase or alkaline phosphatase.

As is appreciated by those skilled in the art, ELISAs can be performed in a number of assay formats. In one ELISA format, a host sample, e.g., a patient body fluid sample, is incubated on a solid support, e.g., the wells of a microtiter plate, or a polystyrene dish, to which the proteins in the sample can bind. Any free protein binding sites on the dish are then blocked by incubating with a non-specific protein such as bovine serum albumin. The monoclonal antibody is then added to the solid support, e.g., the wells or the dish, and allowed to incubate. During the incubation time, the monoclonal antibodies attach to any EGFR ECD or HER-2/neu ECD polypeptides that have attached to the polystyrene dish.

All unbound monoclonal antibody is washed away using an appropriate buffer solution. The reporter antibody, e.g., linked to horseradish peroxidase, is added to the support, thereby resulting in the binding of the reporter antibody to any monoclonal antibody which has bound to EGFR ECD or HER-2/neu ECD present in the sample. Unattached reporter antibody is then washed away. Peroxidase substrate is added to the support and the amount of color developed in a given time period provides a measurement of the amount of EGFR ECD or HER-2/neu ECD that is present in a given volume of patient sample when compared to a standard curve.

In another ELISA format, as described further below and exemplified herein, antibody specific for a particular analyte is attached to the solid support, i.e., the wells of a microtiter plate or a polystyrene dish, and a sample containing analyte is added to the substrate. Detectable reporter antibodies, which bind to the analyte that has bound to the capture antibodies on the support, are then added, after the appropriate incubations and washings, and analyte-antibody complexes are detected and quantified.

In a preferred embodiment, the present invention involves a sandwich type ELISA immunoassay typically performed using microtiter plates. A capture antibody, that can be polyclonal or monoclonal, preferably a monoclonal antibody, that specifically recognizes an epitope in the extracellular portion of EGFR or HER-2/neu is used, along with a labeled detector antibody, e.g., an alkaline phosphatase-labeled antibody, or a horse radish peroxidase-labeled antibody, preferably a monoclonal antibody. The detector antibody also specifically recognizes an epitope on the extracellular protein domain of EGFR, or HER-2/neu. Preferably, the capture antibody does not inhibit EGF binding, and does not cross-react with erbB-2 oncoprotein or human blood group A antigen. Preferably also, the capture antibody does not inhibit binding to HER-2/neu or HER-2/neu ECD. The production of both polyclonal and monoclonal antibodies, particularly monoclonal antibodies that are specific for the ECD of EGFR, or the ECD of HER-2/neu, is performed using techniques and protocols that are conventionally known and practiced in the art, such as described, for example, in the patents to J. Harvey et al., supra.

In a particular embodiment according to this invention, a capture anti-EGFR ECD antibody of the assay method, or a capture anti-HER-2/neu antibody, is immobilized on the interior surface of the wells of the microtiter plate. (see, e.g., Examples 1A and 1B and Example 2). To perform the assay, an appropriate volume of sample is incubated in the wells to allow binding of the antigen by the capture antibody. The immobilized antigen is then exposed to the labeled detector antibody. Addition of substrate to the wells, if the detectable label is alkaline phosphatase, for example, allows the catalysis of a chromogen, i.e., para-nitrophenylphosphate (pNPP), if the label is alkaline phosphatase, into a colored product. The intensity of the colored product is proportional to the amount of EGFR that is bound to the microtiter plate.

Standards are used to allow accurate quantitative determinations of EGFR ECD or HER-2/neu (or HER-2/neu ECD) in the samples undergoing analysis. A microtiter plate reader simultaneously measures the absorbance of the colored product in the standard and the sample wells. Correlating the absorbance values of samples with the standards run in parallel in the assay allows the determination of the levels of EGFR ECD or HER-2/neu ECD in the sample. Samples are assigned a quantitative value of EGFR ECD in nanograms per milliliter (ng/ml) of serum, plasma, other body fluid, or cell culture fluid.

For the embodiment in which EGFR ECD levels are specifically analyzed or assessed in combination with HER-2/neu levels, antibodies directed against HER-2/neu are used for HER-2/neu detection and measurement. In addition, immunoassays for the determination of HER-2/neu in samples, preferably serum samples, are employed. (Example 1B).

According to the present invention, a method is provided that permits the identification and/or monitoring of patients who will benefit from both traditional and non-traditional treatments and therapies for a variety of cancers, particularly those cancers or neoplasms associated with the overexpression of EGFR. The present invention thus embraces testing, screening and monitoring of patients undergoing anti-cancer or anti-neoplastic treatments and therapies, such as those involving small molecule inhibitors of EGFR, anti-EGFR antibody-based immunotherapies, used alone, in combination with each other, and/or in combination with anti-cancer drugs, anti-neoplastic agents, chemotherapeutics, radiation, and/or surgery, to treat cancer patients.

Also according to the present invention, the combined testing and monitoring of EGFR levels and HER-2/neu levels, particularly the ECD of these receptor proteins, in a cancer patient sample, and the assessment of a concomitant decrease in the levels of EGFR and elevation in the levels of HER-2/neu in the samples, provide a valuable tool for the physician or clinician to quickly determine that aggressive forms of treatments, including both traditional and non-traditional treatments and therapies, should be used to fight the cancer. This combined analysis is especially applicable to breast cancer and metastatic breast cancer patients, as the finding of EGFR level decreases and HER-2/neu level increases in the sera of these types of patients, relative to control values, is indicative of a shorter time to progression and a shorter overall survival time. Armed with this information, the treatment provider or facility can choose to administer one or more treatments or treatment regimens swiftly and aggressively in an attempt to counteract the disease. Thus, testing, screening and monitoring of patients undergoing anti-cancer or anti-neoplastic treatments and therapies, such as those involving small molecule inhibitors of EGFR and/or HER-2/neu, anti-EGFR and/or anti-HER-2/neu antibody-based immunotherapies, used alone, in combination with each other, and/or in combination with other anti-cancer drugs, anti-neoplastic agents, chemotherapeutics, radiation, and/or surgery, to treat cancer patients, are all part of the embodiment in which both EGFR and HER-2/neu values are co-determined in patient samples.

It is to be understood that decreases in EGFR levels and elevations in HER-2/neu levels are typically determined by comparison to controls. For example, a decreased EGFR level is one which is less than the normal control range of EGFR, i.e., 45-78 ng/ml. Similarly, an increased HER-2/neu level is one which is greater than normal HER-2/neu levels of <15 ng/ml. In particular, shorter time to progression and shorter overall survival were found in women with metastatic breast cancer who had decreased EGFR levels (less than control range) and elevated HER-2/neu levels, compared with one or more controls comprising women who had (a) normal EGFR levels (45-78 ng/ml) and normal HER-2/neu levels (<15 ng/ml); (b) normal EGFR levels, but elevated HER-2/neu levels; or (c) decreased EGFR levels, but normal HER-2/neu levels.

An advantage of the present invention is the ability to identify and monitor, or screen over time, those patients who can benefit from one, or several, of the available therapies, and preferably, to monitor patients receiving one or a combination of therapies over time; to determine how the patient is faring from the treatment(s); to determine if a change, alteration, or cessation of treatment is warranted; to determine if the patient's disease has been reduced, ameliorated, or lessened; and to determine if the patient's disease state or stage has advanced so as to become metastatic or invasive. The cancer treatments embraced herein also include surgeries to remove or reduce in size a tumor, or tumor burden, in a patient. Accordingly, the methods of the invention are useful to monitor patient progress and disease status post-surgery.

The identification of the correct patients for a cancer therapy by employing the methods according to this invention can provide an increase in the efficacy of the treatment and can avoid subjecting a patient to unwanted and life-threatening side effects of the therapy. By the same token, the ability to monitor a patient undergoing a course of therapy using the method of the present invention can determine whether a patient is adequately responding to therapy over time, to determine if dosage or amount or mode of delivery should be altered or adjusted, and to ascertain if a patient is improving during therapy, is regressing or is entering a more severe or advanced stage of disease, including invasion or metastasis.

A method of monitoring according to this invention reflects the serial, or sequential, testing or analysis of a cancer patient by testing or analyzing the patient's body fluid sample over a period of time, such as during the course of treatment or therapy, or during the course of the patient's disease. For example, in serial testing, samples, e.g., blood or plasma, are taken from the same patient at different times for the purpose of observing, checking, or examining the levels of EGFR ECD in the patient by measuring the levels of this analyte during the course of treatment, and/or during the course of the disease, according to the method of the invention. Such serial testing can also include the assessment, e.g., repeated or serial testing, of EGFR and HER-2/neu levels in combination, as has been described above.

Similarly, a patient can be screened over time to assess the levels of EGFR ECD, as well as EGFR ECD and HER-2/neu levels in combination, in a body fluid sample for the purposes of determining the status of his or her disease and/or the efficacy, reaction, and the patient's response to cancer or neoplastic disease treatments or therapies that he or she is undergoing. It will be appreciated that one or more pretreatment sample(s) is/are optimally taken from a patient prior to and at the start of a course of treatment or therapy to assist in the analysis and evaluation of patient progress and/or response at one or more later test points during the period of time that the patient is receiving treatment and undergoing clinical and medical evaluation.

In monitoring a patient's EGFR ECD levels, or the combination of EGFR ECD and HER-2/neu levels, over a period of time, which may be days, weeks, months, and in some cases, years, or various intervals thereof, the patient's body fluid sample, e.g., serum or plasma, is collected at intervals, as determined by the practitioner, such as a physician or clinician, to determine the levels of EGFR ECD, or the combination of EGFR ECD and HER-2/neu levels, in the cancer patient compared to the levels of this analyte in normal individuals over the course or treatment or disease. For example, patient samples can be taken and monitored every month, every two months, or combinations of one, two, or three month intervals according to the invention. Quarterly, or more frequent patient monitoring is advisable. In addition, the EGFR ECD levels, or a combination of EGFR ECD and HER-2/neu levels, of the cancer patient obtained over time can be conveniently compared with each other, as well as with the EGFR ECD values, or a combination of EGFR ECD and HER-2/neu values, of normal controls, during the monitoring period, thereby providing the patient's own EGFR ECD values, or a combination of EGFR ECD and HER-2/neu values, as an internal, or personal, control for long-term EGFR ECD monitoring, or long-term monitoring of EGFR ECD and HER-2/neu levels, in combination.

At the times tested, the levels of EGFR ECD found in the patient are compared with the levels of EGFR ECD in normal individuals to determine treatment or disease progress or outcome. The patient's later sampled EGFR ECD levels can also be compared with his or her prior levels during the testing period. As described herein, following the course of treatment or disease, the determination of a decrease in the EGFR ECD levels in the cancer patient over time compared to the levels of EGFR ECD in normal individuals reflects the ability to determine disease severity, or the course of a patient's therapy or outcome. Similarly, in the aspect in which both EGFR ECD levels and HER-2/neu levels are determined in combination, HER-2/neu levels are also compared with those of normal individuals, or with the levels of other cancer patients, as described herein.

EGFR ECD EMBODIMENTS

For a variety of cancers, e.g., lung cancer, prostate cancer, ovarian cancer, colon cancer and breast (mammary) cancer, a decrease in the levels of EGFR ECD in the cancer patient's sample, e.g., serum, relative or compared to the levels of this analyte determined in normal controls following performance of the method of the invention is indicative of disease progression or a more advanced stage of the cancer. A decrease in the level of the EGFR ECD analyte in cancer patients is determined by comparing the value obtained from analyzing cancer patient samples to the normal control range values. In performing the method of the present invention, any value outside of the normal control range is considered increased or decreased, depending on the value. The normal range is the normal mean (i.e., average) value plus/minus ($\pm$) two standard deviations.

In an embodiment of this invention, in monitoring a patient over time, an increase or elevation in the levels of a patient's EGFR ECD analyte from a former decreased level to a level at or near to the level of the analyte found in normal individuals is indicative of treatment progress or efficacy, and/or disease improvement, remission, tumor reduction or elimination, and the like. Likewise, in all of the methods described in the embodiments of this invention, a determination of an increase in the patient's EGFR ECD levels relative to past levels and to normal levels; or the return of a patient's EGFR ECD levels to, or approximately to, the levels of EGFR ECD found in normal individuals, provides a further advantage of the methods of the invention, such that a patient's improvement, recovery or remission, and/or treatment progress or efficacy, is able to be ascertained following performance of the method by observing a change from decreased to increased levels of EGFR ECD compared to normal EGFR ECD levels during a monitoring period.

In another embodiment, a cancer patient's sample is analyzed in accordance with the methods of this invention to determine if there is a decrease in the EGFR ECD levels compared with the levels of EGFR ECD found to be a normal range of EGFR ECD in the serum of normal, cancer-free individuals. (Table 1). According to the present invention, normal values of EGFR ECD in serum have been determined to allow a reliable and standardized comparison between the levels of the EGFR ECD analyte in normal controls and in cancer patients The normal values for the EGFR ECD analyte in serum are presented in the following Table 1:

TABLE 1

| Sample Type | Number Tested | Mean Normal Value of EGFR ECD in Serum | Range of Normal Values of EGFR ECD in Serum* |
|---|---|---|---|
| Normal Males | n = 110 | 62 ng/ml | 46-79 ng/ml |
| Normal Females | n = 111 | 61 ng/ml | 45-78 ng/ml |
| Normal Males + Normal Females | n = 221 | 62 ng/ml | 45-78 ng/ml |

*All normal ranges and cutoff values represent the mean ± two standard deviations (mean ± 2 SD)

The EGFR normal values, such as those provided in Table 1, can be expressed in femtomoles (fmole). For the EGFR ECD, 1 ng=9.09 fm, and 1 ng/mL=9.09 fm/mL. Thus, the mean value of 61 ng/ml=555.10 fm/mL; 62 ng/mL=564.20 fm/mL, etc. In addition, in Table 1, 62 ng/ml constitutes the mean value of EGFR ECD in serum; 45 ng/ml is the cutoff value for the lower limit of normal, and 78 ng/ml is the cutoff value for the upper limit of normal.

Another embodiment of the present invention encompasses a method of monitoring a cancer patient's course of disease, or the efficacy of a cancer patient's treatment or therapy, in which the patient has a cancer associated with overexpression of EGFR. Preferably, the patient has a cancer selected from cancer of the breast, colon, bladder, lung and prostate. The patient's treatment or therapy can involve an anti-EGFR-specific treatment or therapy, or more traditional therapies, such as hormone therapy, chemotherapeutic drug therapy, radiation, or a combination of any of the foregoing. The method involves measuring levels of EGFR ECD in a body fluid sample of the cancer patient, preferably a serum or plasma sample, and determining if the levels of the EGFR ECD in the patient's sample are decreased compared to the levels of the EGFR ECD in normal controls during the course of disease or treatment. For EGFR ECD determinations, serum and plasma levels of this analyte are comparable. Accordingly, normal ranges for an analyte in different body fluid sample types are preferably specific to the sample type being analyzed.

In accordance with this method, a decrease in the levels of the EGFR ECD in the cancer patient compared to the levels of the EGFR ECD in normal controls is indicative of an increase in stage, grade, severity, advancement, or progression of the patient's cancer and/or a lack of efficacy or benefit of the cancer treatment or therapy provided to the patient during a course of treatment, i.e. poor treatment or clinical outcome. As a specific example, for the purpose of comparison of EGFR ECD in cancer patients and normal individuals in the method, the normal value of EGFR ECD is in the range of approximately 45-78 ng/ml. Thus, the determination of a decrease in EGFR ECD level compared to this normal range in a cancer patient alerts the practitioner to a more serious disease stage or grade, or to a lack of effectiveness of the patient's cancer treatment. In the practice of the present method, any value outside of the normal control range is considered increased or decreased. The normal range is the normal mean (i.e., average) value plus/minus (±) two standard deviations.

As will be understood by the skilled practitioner in the art, the monitoring method is preferably performed in a serial or sequential fashion, using samples taken from a patient during the course of disease, or a disease treatment regimen, (e.g., after a number of days, weeks, months, or occasionally, years, or various multiples of these intervals) to allow a determination of disease progression or outcome, and/or treatment efficacy or outcome. If the sample is amenable to freezing or cold storage, samples may be taken from a patient (or a normal individual) and stored for a period of time prior to analysis.

In a particular embodiment of this invention, the above method is performed using body fluid samples, preferably serum samples, from ovarian cancer patients to ascertain the levels of EGFR ECD in the sera of the ovarian cancer patients having stage I-IV ovarian cancers compared to the levels of EGFR ECD in normal individuals. For normal females, and normal male and females, the normal range EGFR ECD values are 45-78 ng/ml in serum. For normal females, the mean normal value for serum EGFR ECD levels is 61 ng/ml (±2 SD); for normal males, the mean normal value for serum EGFR ECD levels is 62 ng/ml (±2 SD).

According to the present invention, as the stage of ovarian cancer increased (i.e., from benign to stage IV), the percentage of sera samples showing a decrease in EGFR ECD levels also increased. As described in Example 2, benign ovarian sera showed 8% of the samples below the normal range for EGFR ECD, while stage I ovarian cancer sera showed 29% of the samples decreased in EGFR ECD levels; stage II ovarian cancer sera showed 50% of the samples decreased in EGFR ECD levels, stage III ovarian cancer sera showed 74% of the samples decreased in EGFR ECD levels and stage IV ovarian cancer sera showed 78% of the samples decreased below the normal value for EGFR ECD. Therefore, the present method allows the outcome of the determination of decreased serum EGFR ECD levels of ovarian cancer patients compared to those of normal individuals to serve as an indicator of severity or advanced grade or stage of ovarian cancer.

In another of its embodiments, the present invention provides a method of monitoring cancer treatment or the clinical response of a cancer patient undergoing cancer treatment, preferably for a cancer or neoplastic disease that is associated with EGFR overexpression. The treatment can involve anti-epidermal growth factor receptor (anti-EGFR) treatment or therapy, such as small molecule inhibitors of EGFR, or anti-EGFR antibodies, or can involve more traditional cancer therapies, or combinations of any of the types of therapies. The method comprises measuring the levels of the ECD of EGFR in a serum or plasma sample of the cancer patient during the course of the patient's cancer treatment and determining if the cancer patient has decreased serum or plasma levels of the ECD of EGFR compared to the serum or plasma levels of the ECD of EGFR as determined for normal individuals for each sample analyzed.

The outcome of cancer treatment of the patient is determined based upon decreased serum or plasma EGFR ECD levels in the patient compared to normal EGFR ECD serum or plasma levels during the course of time that the patient is monitored, where decreased levels of plasma or serum EGFR ECD in cancer patients relative to the normal levels of this analyte correlate with poor treatment or clinical outcome. The method further comprises determining the serum or plasma levels of EGFR ECD after a patient has undergone treatment for a period of time that is deemed by the physician or clinician to allow an adequate determination of efficacy of treatment, and determining by performance of the method whether or not the treated patient's EGFR ECD levels have risen to, or near to, those of normal individuals. An increase or rise in the patient's EGFR ECD levels following a course of treatment or therapy indicates progress and/or efficacy of the cancer treatment or therapy.

An especially heartening determination for the patient and the physician or clinician is the observation of a change in the patient's EGFR ECD levels during a patient's course of treatment, i.e., from a finding of decreased levels of EGFR ECD in pretreatment or early treatment patient samples to a finding in the patient of increased EGFR ECD levels, or levels of this analyte that are at, or close to, the respective level of EGFR ECD determined in normal individuals. Such a finding can reflect, among other things, patient improvement from the treatment or therapy, successful treatment outcome, and/or a change to a less serious stage or phase of disease.

In another of its embodiments, the present invention encompasses a method of monitoring disease severity or progression of a cancer patient. The method comprises measuring levels of the EGFR ECD in a body fluid sample, e.g., a serum or plasma sample, of the cancer patient and determining if the cancer patient has decreased levels of the EGFR ECD compared to the levels of the EGFR ECD in normal individuals. Cancer severity or progression is monitored in the patient based upon decreased EGFR ECD levels in the patient's body fluid sample compared to normal EGFR ECD levels in normal individuals. According to this method, the most severe cancer stage correlates with the lowest levels of plasma or serum EGFR ECD relative to the normal control levels of the EGFR ECD analyte. Also in accordance with the method of this embodiment, the normal EGFR ECD level is in the range of about 45 ng/ml to about 78 ng/ml, with a normal mean value of EGFR ECD in males of about 62 ng/ml±2 SD, and a normal mean value of EGFR ECD in females of about 61 ng/ml±2 SD.

In yet another related embodiment, the present invention provides a method of monitoring cancer treatment, or efficacy thereof, in a cancer patient undergoing such treatment. The method involves measuring the levels of EGFR ECD in a body fluid sample of the cancer patient and determining if the level of EGFR ECD in the patient decreases during the cancer treatment compared to the level of EGFR ECD found in normal controls, where a decrease in the EGFR ECD levels in the cancer patient compared to the levels of EGFR ECD in the normal controls during the monitoring period indicates one or more of the following: (i) cancer progression; (ii) a more severe stage of the cancer; or (iii) lack of response by the patient to the cancer treatment.

In addition, if, during the course of monitoring the levels of EGFR ECD in the patient undergoing treatment, a change in the EGFR ECD levels of the patient is observed, such that the patient's EGFR ECD levels are increased or elevated to or near to normal values of the EGFR ECD, after having monitored a decrease in these levels for a prior period of time during treatment, an assessment can be made as to one or more of the following: (i) the patient is progressing well on the treatment, (ii) the treatment is effective; (iii) the patient is favorably responding to the treatment; and/or (iv) the patient's cancer is not advancing, or has been ameliorated or eliminated by the treatment.

In accordance with the present invention, such a method of monitoring and assessment of the EGFR ECD levels during a patient's course of treatment or therapy, compared with normal levels of EGFR ECD, can provide the physician or clinician with a determination of a cancer patient's progress or lack thereof, as a consequence of a particular treatment or therapy. Such a determination allows tailoring of the cancer or anti-neoplastic treatment or therapy to better or more aggressively attack (or treat) a cancer and to select the most appropriate treatment, or course of treatment or therapy for an individual patient. This approach also allows the practitioner to determine whether dosage or mode of administration should be altered, or whether the drug regimen should be modified, for example, by combining therapies or discontinuing therapies, to try to achieve a more effective overall treatment and outcome for the patient. As an example, if it is determined by way of practicing the present invention that a patient has a high likelihood of relapse (due to the monitoring of a continued decrease in EGFR ECD levels compared with normal levels of the EGFR ECD analyte over a number of test intervals), the patient can be treated more rigorously, such as by using systemic chemotherapy and/or radiation therapy, or other treatment combinations. Similarly, when the levels of EGFR ECD monitored by the present methods are determined to increase over time, i.e., to levels at or close to those of normal controls, less aggressive therapies can be decided upon. The ability to select a personalized course of therapy or treatment regimen, i.e., to be able to choose a less aggressive treatment at or close to the start of treatment, or to alter treatment from aggressive to less aggressive at a time prior to the conventional end of a treatment regimen on the basis of the monitoring analysis methods of this invention, can provide less anguish and suffering for the patient on both an emotional and physical level.

Embodiments Encompassing the analysis of EGFR ECD levels and the analysis of EGFR ECD levels in combination with HER-2/neu levels In a more preferred embodiment, the present invention embraces a method of monitoring, screening, or examining over time the outcome and/or clinical benefit of cancer treatment or therapy in a patient having a metastatic cancer, for example, metastatic breast cancer. The breast cancer can further involve overexpression of epidermal growth factor receptor (EGFR). This method embraces determining if a body fluid sample from a cancer patient has decreased levels of EGFR ECD compared to the levels of EGFR ECD in normal controls. Preferably, the body fluid sample is a serum or plasma sample. The method can additionally, or optionally, also involve a combined determination of both EGFR and HER-2/neu levels in the patient sample. Accordingly, the method comprises determining if a body fluid sample from the cancer patient, preferably a serum sample, has decreased levels of EGFR and increased levels of HER-2/neu, in combination, compared to the levels of these analytes in normal controls, or other controls, as has been described hereinabove. It is to be understood that levels of the extracellular domains of EGFR ECD and HER-2/neu can be assessed in the method.

Performance of the method using a patient's sample before treatment (i.e., pretreatment), at the start of treatment and at different time intervals during treatment allows the determination that the patient having decreased EGFR ECD levels compared to the EGFR ECD levels of normal controls (or having a combination of decreased EGFR ECD levels and increased HER-2/neu levels compared to the levels of these proteins in control individuals) is likely to have an unsuccessful outcome of cancer treatment or therapy, as characterized by reduced clinical benefit, shorter time to progression, and shorter overall survival, based upon the determination of the decreased levels of EGFR ECD in the patient compared with normal control individuals, (Example 3), or based upon the determination of a combination of decreased levels of EGFR ECD in the patient compared with control individuals and of increased HER-2/neu levels in the patient compared with control individuals.

In another preferred embodiment of this invention, a patient sample, preferably a serum sample, is tested or screened for its levels of EGFR and its levels of HER-2/neu, in combination, in the sample. The levels of these two analytes are assessed in combination in order to determine and prognose patient population risk, as well as patient outcome and survival. The testing and screening method is particularly applicable to breast cancer and metastatic breast cancer patients. As has been described and demonstrated, a determination of a decrease in the levels of EGFR and an elevation in the levels of HER-2/neu in a patient sample, relative to control values, is highly correlated with poor prognosis and survival outcome.

Serial testing of patients to examine whether alterations or reversals in the levels of EGFR and HER-2/neu have occurred, for example, following or during treatment or therapy regimens, can be carried out to determine if changes or modifications of patients' treatment or therapy should be considered or undertaken, or to assess patient progress, or lack thereof, during treatment. Thus, if it is determined concomitantly that a patient's serum EGFR levels have increased, or are at normal levels, relative to control levels, and that the patient's serum HER-2/neu levels have decreased relative to control levels, or are at normal levels, following a course of treatment or therapy, the positive and encouraging progress and results of the treatment or therapy can be assessed. Alternatively, lack of progress associated with treatment or therapy results can also be determined by virtue of examining the levels of EGFR and HER-2/neu, in combination, in patient samples over time.

It is to be understood that in all of the embodiments describing the methods according to the present invention, the monitoring of a cancer patient for disease progression or outcome, or for cancer treatment or therapy efficacy or outcome, can include the analysis of a pretreatment sample taken from the patient at a first point in time, as well as patient samples taken at second, third, fourth, or subsequent time points, during the course of disease or during a cancer or anti-neoplastic treatment or therapy regimen, or a combination of treatment or therapy regimens. The resulting EGFR ECD levels, or the combination of EGFR ECD and HER-2/neu levels, in samples taken from all test points can be compared to normal EGFR ECD levels, or to control EGFR ECD and HER-2/neu levels; or among each other, i.e., the patient's own samples can be compared to each other, and in view of the other control parameters as described herein, to determine disease status and/or treatment effectiveness.

EXAMPLES

The following examples describe specific aspects of the invention to illustrate the invention and provide a description of the present methods for those of skill in the art. The examples should not be construed as limiting the invention, as the examples merely provide specific methodology useful in understanding and practice of the invention and its various aspects.

Example 1

A. Enzyme Linked Immunoassay (ELISA) to Measure Levels of EGFR ECD in a Body Fluid Sample Cell culture fluids are centrifuged to remove all particulate matter. After centrifugation, the samples can be analyzed without further treatment, or stored at −70° C. for future analysis. Cell culture supernatants are analyzed at a range of concentrations to assure that values in the positive cultures, e.g., A431 cells, fall on the standard curve. Maintenance of optimal pH is important for sample incubation; therefore, a starting dilution of at least 1:5 of the culture supernatant in the sample diluent is necessary for the ELISA immunoassay (Bayer Diagnostics/Oncogene Science EGFR Microtiter ELISA, Cambridge, Mass.). Two-fold dilutions in sample diluent from 1:5 to 1:160 provide useful results. The calculation of EGFR recovery in dilutions other than 1:50 require correction as follows: each result is multiplied by 50; this result is divided by the dilution factor for each point tested. For example, a 1:5 dilution of culture fluid reports directly from the standard curve at 10 ng/ml. 10×50/5=100 ng/ml in undiluted fluid.

For serum or plasma samples, the initial concentration to be analyzed should not exceed a concentration of 2% (e.g., a 1:50 dilution of specimen in sample diluent). For example, 0.020 ml of serum or plasma sample can be diluted into 0.980 ml of sample diluent and 100 µl added to the wells of the microtiter plate.

With regard to sensitivity, the Bayer Diagnostics/Oncogene Science EGFR Microtiter ELISA detects 0.25 ng/ml of EGFR analyte (e.g., EGFR ECD) in a sample diluent matrix. The signal of the 0.25 ng/ml standard is approximately two times the zero signal. In addition, the EGFR ECD ELISA is specific for the detection of EGFR ECD; for example, HER-2/neu p105 is not detected, even when tested at levels that are ten-fold higher than the level 6 standard in the assay as described below.

Detailed Protocol

The EGFR Microtiter ELISA kit (commercially available from Bayer Diagnostics/Oncogene Science, Cambridge, Mass.) used in this Example has 96 wells designed as removable strips (12 strips of 8 wells) so that the assay can be performed on multiple occasions, if desired. The wells are pre-coated with anti-human EGFR ECD monoclonal antibody. (see, U.S. Pat. No. 5,344,760 to Harvey et al.). A standard curve is required for each separate assay. Both the standards and the test samples were assayed in duplicate. For greater accuracy, each sample was tested at more than one concentration. Disposable pipette tips and clean reagent troughs were used for all transfers to avoid cross-contamination of reagents and samples. The contents of the EGFr Microtiter ELISA assay manual (Bayer Diagnostics/Oncogene Science, Cambridge, Mass.) are hereby incorporated by reference herein in their entirety.

The EGFR standards are housed in six separate vials containing EGFR ECD (p110) obtained from the supernatant of A431 cells. A431 (ATCC #CRL 1555) is a human epidermoid carcinoma cell line that expresses a 50- to 100-fold excess of EGFR and produces a shortened transcript of the EGFR gene that encodes the ECD (p110). (A. L. Ullrich et al., 1984, *Nature*, 307:418-425; R. N. Fabricant et al., 1977, *Proc. Natl. Acad. Sci. USA*, 74:565-569; M. M. Wrann et al., 1979, *J. Biol. Chem.*, 254:8083-8086). Standards are calibrated using several independent quantitative amino acid analyses of immunoaffinity purified EGFR and are labeled with values that are 50-fold greater than the actual vialed dosage. Assigning the label values to a standard curve obviates the need to correct the reported dose for a 1:50 diluted sample (2% serum in buffer). As provided in the Bayer Diagnostics/Oncogene Science EGFR ECD ELISA kit, standard 6 contained EGFR p110 at 300 ng/ml; standard 5 contained EGFR p110 at 200 ng/ml; standard 4 contained EGFR p110 at 125 ng/ml; standard 3 contained EGFR p110 at 60 ng/ml; standard 2 contained EGFR p110 at 12.5 ng/ml; and standard 1 contained EGFR p110 at 0 ng/ml.

For EGFR ECD determinations performed in accordance with the EGFR ECD ELISA of this Example, the standard curve runs from 12.5 to 300 ng/mL, i.e., 113.6 to 2727 fm/mL.

8-well strips were selected from the microtiter plate; the remaining unused strips were saved for subsequent use. In some cases, the entire plate was used. A working 1× solution of platewash buffer, as provided in the Bayer Diagnostics/Oncogene Science EGFR Microtiter kit, was prepared by adding one part platewash concentrate to 19 parts of deionized water and mixing well. The total volume required depended on the washing method used. Approximately 1 liter of the wash buffer was needed to prime an automated washer and run one microtiter plate. The platewash buffer was freshly prepared on the day of use.

Samples, standards and other kit reagents were warmed to room temperature prior to addition to the microtiter plate wells and starting the assay. Diluted body fluid samples, i.e., test patient sera, were added in duplicate to the wells of the plates, along with each of six EGFR standards (0 to 300 ng/ml) in duplicate, by pipetting 100 µl into the appropriate wells. Standard 0 was added to one additional well of each microtiter plate used, for the determination of the substrate blank. When sample dilution was necessary, sample diluent (BSA, mouse IgG and 0.09% sodium azide) as supplied was used. Unused standards were stored at 4° C. After sample had been added, the wells were covered with plastic wrap or plate sealer and the samples were incubated at 37° C. for 1.5 hours. During this time, the working conjugate was prepared by diluting an appropriate volume of conjugate concentrate (50× alkaline phosphatase-labeled anti EGFR ECD monoclonal antibody) into conjugate diluent (buffered solution, pH 7.0 containing BSA and 0.09% sodium azide), as supplied and according to the directions provided in the kit.

After the incubation, the plastic wrap or plate sealer was removed, and the wells were washed using 300 µl per well of plate buffer wash in six cycles, as supplied and directed in the kit. The plates were washed for three cycles, rotated 180°, and washed for three more cycles. Thereafter, 100 µl of working conjugate were added to all of the wells, except for the substrate blank well, which was left empty. The wells were covered with a fresh piece of plastic wrap or plate sealer and the conjugate was incubated at room temperature (18-27° C.) for 30 minutes. Next, 100 µl of substrate reagent (pNPP) was dispensed into a clean reagent trough and allowed to reach room temperature. The wells were again washed as described above, without allowing the plates to dry out. Immediately after washing, 100 µl of pNPP substrate were added to all of the wells and the plates were covered with plastic wrap or plate sealer. The plates were incubated with substrate at room temperature (18-27° C.) for 45 minutes. Following this incubation, stop solution (100 µl; EDTA solution) was added to each of the wells and absorbance was measured in each well using a spectrophotometric plate reader at a wavelength of 405 nm. The plate wells were read within 15 minutes of adding the stop solution for optimum color development.

The antibodies used in the EGFR Microtiter ELISA (Bayer Diagnostics/Oncogene Science, Cambridge, Mass.) specifically recognize the extracellular, ligand-binding domain of the EGF receptor. This form of EGFR has a molecular weight of approximately 110 kDa. The standards in the kit are calibrated in nanograms, which take into account the 110 kDa molecular weight form of EGFR ECD that is detected in serum. The standards are prepared from a naturally-occurring form of the 110 kDa EGFR.

To evaluate the results obtained from the Example 1 EGFR ECD ELISA, the absorbance values were averaged for each standard and sample dilution to arrive at the mean absorbances. The concentration of unknowns was interpolated from the standard curve. A variety of microplate reader software packages are available for analysis of microplate data, e.g., SoftmaxPro™ (Molecular Devices Corporation, Sunnyvale, Calif.; KC4™, BioTek Instruments, Inc. Winooski, Vt.) that simplify the process. A quadratic curve fitting algorithm (second order polynomial) was used. The results for the samples were expressed in ng/ml by reading directly from the standard curve concentrations, as directed in the kit manual. For convenience, no mathematical dilution correction was needed for 1:50 diluted samples, since the actual concentration in the standard preparations was at 2% of the labeled dosage, i.e., the standards were pre-diluted at 1:50).

For samples that had OD values exceeding the range of the standard curve, subsequent assay at higher dilutions was necessary. Any such sample result required correcting the value obtained from the assay for any dilution that was higher than 1:50. For example, for a sample dilution of 1:100, the reported result was multiplied by 2 (the dilution correction factor); for a sample dilution of 1:200, the reported result was multiplied by 4 (the dilution correction factor); for a sample dilution of 1:400, the reported result was multiplied by 4 (the dilution correction factor).

The results for cell culture fluids were expressed in ng/ml by correcting the value obtained from the standard curve for the dilution used at that point. The calculation of EGFR recovery in dilutions other than 1:50 required correction. Accordingly, for such cases, each result was multiplied by 50, then divided by the dilution factor for each point tested. For example, a 1:5 dilution of culture fluid reported directly from the standard curve at 10 ng/ml. (10×50/5=100 ng/ml in undiluted fluid).

B. Enzyme Linked Immunoassay (ELISA) to Measure Levels of HER-2/neu in a Body Fluid or Tissue Sample Part B of this Example describes a solid phase, sandwich HER-2/neu Microtiter ELISA for the quantitative determination of HER-2/neu in patient serum, plasma and tissue samples. The ELISA was performed using a kit (HER-2/neu Microtiter ELISA) that is commercially available from Oncogene Science, Bayer Diagnostics, Cambridge, Mass. The Oncogene Science HER-2/neu Microtiter ELISA can detect and quantify both the ECD present in body fluids and the full-length p185, which is typically present in cell lysates obtained from tissue samples. The HER-2/neu Microtiter ELISA utilizes monoclonal antibodies that specifically bind epitopes present on both the ECD p105 and the p185 molecules. (S. J. McKenzie et al., 1989, *Oncogene*, 4:543-548).

The HER-2/neu Microtiter ELISA detects 44 pg (0.24 femtomoles) of HER-2/neu p185 per mL in a sample preparation, and 1.5 ng of p105 per mL of serum. Sensitivity is defined as the assay signal midway between the 0 and 2.5 ng standard. (HER-2/neu Microtiter ELISA product brochure). When tested against fm/mL levels of EGFR protein (p170), the HER-2/neu ELISA showed no cross-reactivity; minimal to no cross-reactivity was observed using cell lines having low to no HER-2/neu protein expression.

The standards in the HER-2/neu Microtiter ELISA are prepared from the p105 ECD of the HER-2/neu protein, and have been calibrated in ng/mL. The standards are conveniently provided for p105 determinations of 1:50 diluted serum samples, but are not appropriate, in this configuration for direct determination of tissue lysate results, (see below, HER-2/neu Microtiter ELISA, Oncogene Science, Bayer Corporation, Cambridge, Mass.).

Briefly, the Oncogene Science HER-2/neu Microtiter ELISA is a sandwich enzyme immunoassay that employs a mouse monoclonal antibody for capture and a different biotinylated mouse monoclonal antibody for the detection of human neu protein. Both the capture and detection reagents specifically bind to the extracellular domain of the neu protein. The capture antibody is immobilized on the interior surfaces of the well of a microtiter plate. To perform the test, an appropriate volume of diluted sample is incubated in the coated well to allow binding of the antigen by the capture antibody. The immobilized antigen is then reacted with the detector antiserum. The amount of detector antibody that is bound to the antigen is measured by binding it with a streptavidin/horseradish peroxidase conjugate, which then catalyzes the conversion of the chromogenic substrate, o-phenylenediamine (OPD) into a colored product. The colored reaction product is quantified by spectrophotometry (490 nm) and is related to the amount of neu protein in the sample.

Serum and plasma samples (and controls), are microcentrifuged to remove flocculent material. Prior to assay, the centrifuged serum and plasma samples and controls are diluted 1:50 (2%) into sample diluent (aqueous solution containing BSA and 0.1% sodium azide, as supplied), mixed thoroughly and added to the microtiter wells in 100 µL aliquots. Duplicate wells of samples and controls are used. One well of the plate is set up with 100 µL of sample diluent for use as a substrate blank. The plate is covered and allowed to incubate for 3 hours at 37° C. Thereafter, the wells are washed in platewash as supplied and 100 µL of detector antibody (biotinylated monoclonal anti-neu protein antibody or anti-HER-2/neu protein antibody in 0.01 M PBS, pH 7.4, protein stabilizer and 0.1% sodium azide) are added to all wells, except for the well containing the substrate blank control. The plates are then covered and incubated for 1 hour at 37° C. During the incubation with the detector antibody, the working conjugate is prepared by diluting the conjugate concentrate (50× streptavidin/horseradish peroxidase in buffer) with conjugate diluent (0.01 M PBS, pH 7.4, BSA and 0.01% chloroacetamide) to a final 1× concentration, depending on the number of microtiter well strips being assayed.

Following incubation with the detector antibody, the microtiter plate wells are washed with platewash and 100 µL of the working conjugate is then added to all of the wells, except for the substrate blank well. The wells are again covered and incubated at room temperature (15° C.-30° C.) for 30 minutes. During the incubation with working conjugate, the working substrate is prepared by dissolving substrate OPD tablets in substrate diluent (0.1 M citrate buffer, pH 5.0, and 0.01% $H_2O_2$). The substrate tablet/solution is vortexed vigorously to ensure complete dissolution. Once prepared, the working substrate is used within 30 minutes and is protected from exposure to light.

The microtiter wells are washed with platewash after the incubation in working conjugate. Working substrate (100 µL/well) is then added to all of the wells, including the substrate blank well. The wells/plate are covered and the wells/plate are incubated in the dark at room temperature (15° C.-30° C.) for 45 minutes. Stop solution (aqueous solution of 2.5 N $H_2SO_4$) is added to each well to stop the reaction. Absorbance at 490 nm is read within 30 minutes.

Results obtained from the HER-2/neu Microtiter ELISA using serum or plasma samples are compared with standards and controls as supplied in the kit (Oncogene Science, Bayer Diagnostics, Cambridge, Mass.). The antibodies comprising the assay recognize the extracellular, ligand-binding domain of the neu protein (W. P. Carney et al., 1991, *J. Tumor Marker Oncol.*, 6:53-72; S. J. McKenzie et al., 1989, *Oncogene*, 4:543-548). This ECD form of HER-2/neu has been identified with a molecular weight of about 105 kDa. The standards in the kit are calibrated in nanograms, which take into account the molecular weight of the ECD form found in serum, and are prepared from a recombinant form of the 105 kDa portion of HER-2/neu.

The absorbance values for each standard, control and test sample dilution are averaged to obtain the mean absorbances. To prepare a standard curve, the mean absorbance for each standard is plotted on the y-axis versus the concentration of neu protein (ng/mL) on the x-axis. The concentration of neu protein is determined for each sample dilution tested by interpolation from the standard curve. Software packages are available for this process, e.g., Softmax™, Molecular Devices, Sunnyvale, Calif.; and KinetiCalc™, Bio-Tek Instruments, Inc., Winooski, Vt.). A quadratic curve fit (second order polynomial) algorithm is used.

Results from the samples undergoing testing are expressed in ng/mL by reading from the standard curve as designated. No mathematical dilution correction is typically needed for the samples diluted 1:50, as the actual concentration of the standard preparations is at 2% of the labeled dosage. For samples that yield OD values exceeding the range of the standard curve, subsequent assay at greater dilutions are necessary. If further dilutions are made, the value obtained from the assay must be corrected for any dilution beyond 1:50, for example, a reported result is multiplied by a dilution correction factor of 2 for a sample dilution of 1:100; a reported result is multiplied by a dilution correction factor of 4 for a sample dilution of 1:200; and a reported result is multiplied by a dilution correction factor of 8 for a sample dilution of 1:400.

For tissue specimens, a cytosol is prepared; a sample of the homogenate is withdrawn just before ultracentrifugation and used for the measurement of neu protein after further processing as described in the kit brochure. (Oncogene Science, Bayer Diagnostics, Cambridge, Mass.). Briefly, for tissue sample preparation, a frozen tissue specimen is weighed and sliced into small pieces. Cold (4° C.) receptor buffer (10 mM Tris-HCl, pH 7.4; 1.5 mM EDTA; 10% glycerol; and 0.1% sodium azide) is added to the pieces of tissue at a buffer:tissue ratio of 10:1 (v/w), e.g., 10 mL buffer is added to 1 g tissue). A protease inhibitor cocktail which can be used contains 0.5 µg/mL leupeptin, 1 µg/mL pepstatin and 0.2 mM pA-PMSF.

The tissue is homogenized on ice using a homogenizer (e.g., Polytron) with two, 25 second bursts at ½ speed (setting 6). Between bursts, the tissue sample homogenate is cooled on ice for 15-20 seconds. An aliquot (50 µL) of the homogenate is mixed with 10 µL of PBS containing 6% Triton X-100 in a microcentrifuge tube, i.e., in a 1:6 dilution, and incubated for 5 minutes at room temperature with mixing. At this point the samples can be used, or stored frozen at −70° C. for at least one month. For immediate use, the homogenate is centrifuged at 15,000 rpm (~14-16,000×g) for 10 minutes in a microcentrifuge and the supernatant is recovered. Protein concentration in the supernatant is measured using conventional methods, e.g., the Micro-BCA assay (P. K. Smith et al., 1985, *Analyt. Biochem.*, 150:76-85; Pierce Chemical Co., Rockford, Ill.); Bio-Rad protein microassay (M. M. Bradford, 1976, *Analyt. Biochem.*, 72:248-254; Bio-Rad Laboratories, Richmond, Va.); or the Lowry method (O. H. Lowry et al., 1951, *J. Biol. Chem.*, 193:265-275).

Prior to the measurement of neu protein levels in the HER-2/neu Microtiter ELISA, the sample is diluted to an appropriate protein concentration. A starting lysate protein concentration of 5 µg/mL in sample diluent is recommended. (HER-2/neu Microtiter ELISA, Oncogene Science, Bayer Corporation, Cambridge, Mass.).

Because the molecular form of HER-2/neu in tissue (full-length p185), is 1.76-fold greater in molecular weight than the form of HER-2/neu in the standards, correction must be made for this discrepancy, as specified in "Adjustment of Results for Lysates", (HER-2/neu Microtiter ELISA manual, Oncogene Science, Bayer Corporation, Cambridge, Mass.). Results are reported in ng of p185 per unit of total protein in the lysate sample (ng p185/mg lysate protein), since sample preparations are assayed at a chosen protein concentration in sample diluent, rather than using a dilution factor.

Example 2

Microtiter Based ELISA to Examine Serum Levels of EGFR in Normal and Cancer Patient Serum Samples Human serum samples were diluted in commercially available ELISA kit sample diluent (Bayer Diagnostics/Oncogene Science EGFR Microtiter ELISA, Cambridge, Mass.) and then analyzed in the EGFr microtiter ELISA, as described in Example 1. A standard curve with standards tested in duplicate was run in each ELISA. All normal sera samples were tested in duplicate by at least two different operators. Mean values were obtained for all samples tested. A total of 110 normal male and 111 normal female sera were tested in order to determine a normal cutoff. The cutoff was defined as the mean value +/− two standard deviations (+/− SD). Cancer patient sera was then analyzed in the EGFR ELISA, with samples tested in duplicate by at least two different operators. All other experimental parameters were as above.

The determination of a normal value was defined as the mean value for the 221 normal sera samples +/− two standard deviations. The results from the cancer sera samples were then compared to the normal range. Any of the cancer sera samples that were above the normal range were considered elevated for EGFR ECD and any of the cancer sera samples that were below the normal range were considered decreased for EGFR ECD.

Using over two hundred normal human serum samples, a normal range was established for EGFR ECD levels using the microtiter-based EGFr ELISA (Bayer Diagnostics/Oncogene Science, Cambridge, Mass.). (FIG. 2). This range was determined by calculating the mean value for normal male and normal female sera samples and adding two standard deviations in order to establish an upper limit of normal EGFR ECD in serum. The range for EGFR ECD in normal male sera was determined to be 46-79 ng/ml, in normal female sera the range was determined to be 45-78 ng/ml and for combined males and females the normal range in serum was found to be 45-78 ng/ml.

Figure 1A:
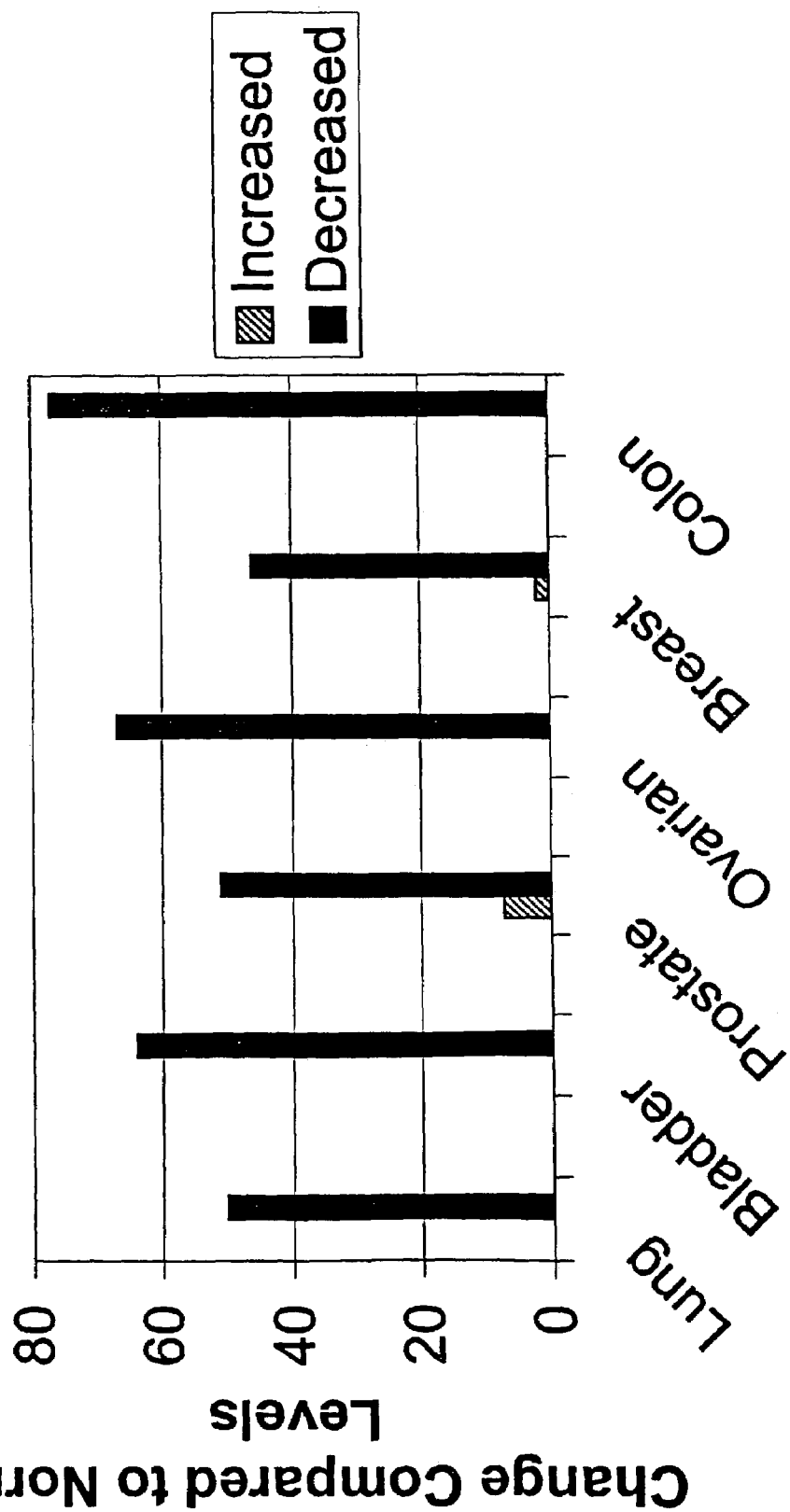

A variety of cancer sera samples were analyzed using the EGFR ECD ELISA detection kit (Bayer Diagnostics/Oncogene Science) and the results were compared with the normal range values described above. The values obtained from the cancer patient sera showed a decrease in all cancer types examined. (FIGS. 1A and 1B). Specifically, 42% of the lung cancer patient sera, 44% of late stage prostate cancer patient sera, 48% of the ovarian cancer patient sera, 67% of the colon cancer patient sera, 56% of the bladder cancer patient sera; 44% of stage III breast cancer patient sera; and 32% of stage IV breast cancer patient sera (46% overall in breast cancer patient sera) showed EGFR ECD levels below the normal range.

Figure 3:
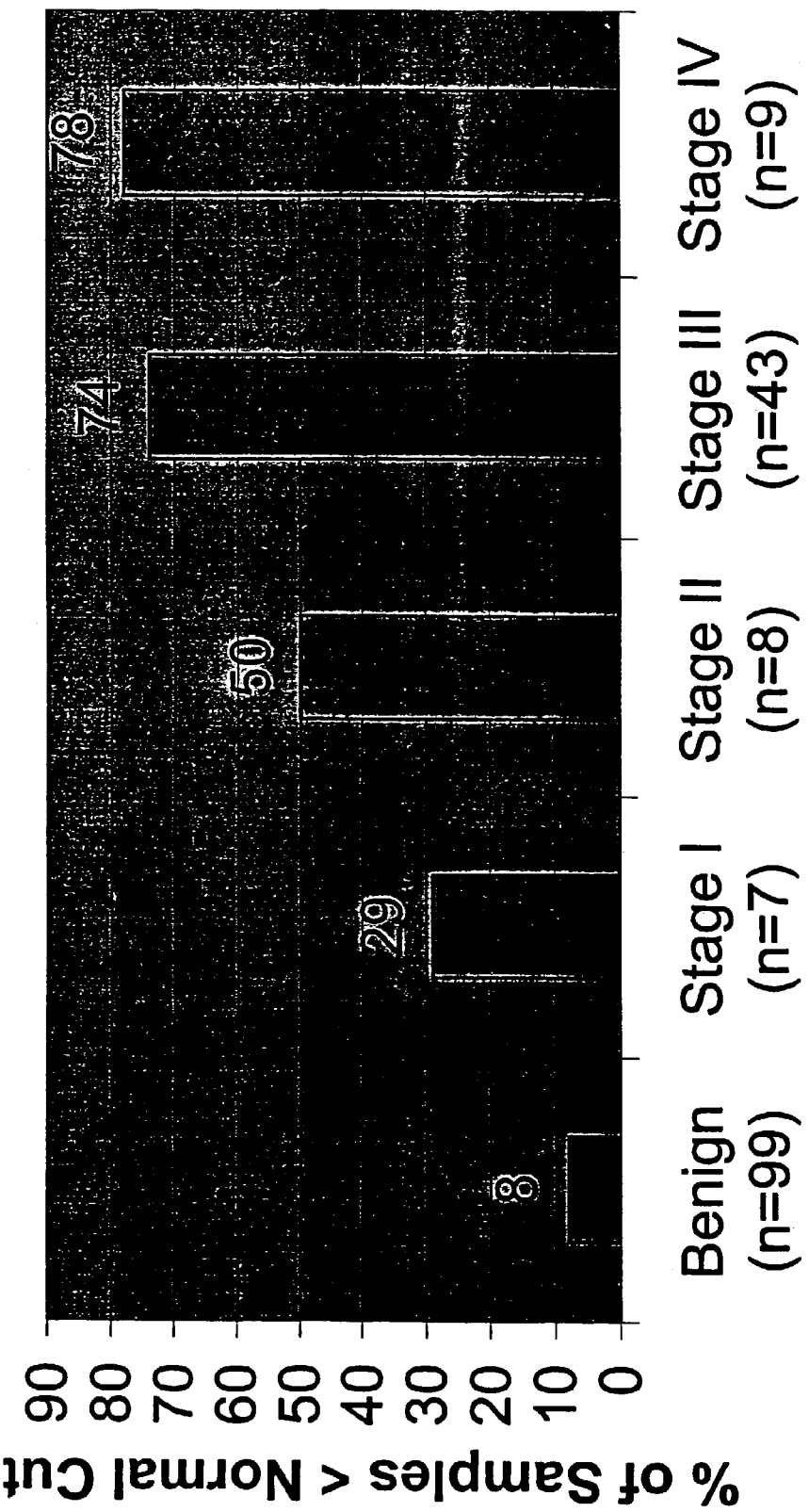
FIG. 3 illustrates the results of the determination of EGFR ECD levels in serum or plasma of patients having ovarian cancer. As depicted, as the stage of ovarian cancer increased, so did the percentage of serum samples which showed decreased EGFR levels, thereby reflecting a correlation of increased stage of ovarian cancer with a decrease in serum EGFR ECD levels in the patient.

In ovarian cancer patients, there were decreases seen in a larger percentage of the samples as the stage of the cancer increased. (FIG. 3). Specifically, benign ovarian sera showed 8% of the samples below the normal range for EGFR ECD, while stage I ovarian cancer sera showed 29% of the samples decreased in EGFR ECD levels; stage II ovarian cancer sera showed 50% of the samples decreased in EGFR ECD levels, stage III ovarian cancer sera showed 74% of the samples decreased in EGFR ECD levels and stage IV ovarian cancer sera showed 78% of the samples decreased below the normal value for EGFR ECD. The normal range of EGFR ECD in normal male and female sera samples was also determined using the microtiter-based ELISA for EGFR ECD (i.e., Bayer Diagnostics/Oncogene Science, Cambridge, Mass.). As can be observed from the results of analyzing sera from a variety of cancer patients, a large percentage of all types of cancer patients' sera showed a significant decrease in EGFR ECD compared with the normal range value of EGFR ECD. In addition, a higher percent decrease frequently correlated with a more advanced stage or grade of cancer.

Example 3

Serum EGFR ECD Levels in Metastatic Breast Cancer Patients

In this Example, serum EGFR ECD was quantified in healthy individuals (controls) and in breast cancer patients using the Bayer Diagnostics/Oncogene Science EGFR Microtiter ELISA, as described in Example 1.

Pretreatment serum was obtained from 265 post-menopausal metastatic breast cancer patients in a multicenter, randomized, double-blind, phase III clinical trial of second line hormone therapy (Fadrozole versus Megestrol acetate). Normal controls consisted of two groups of females: (i) 46 pre-menopausal women having a mean EGFR ECD value of $79.54 \pm 9.87$ ng/ml, with a range (mean$\pm 2$ SD) of from 59.80-99.28 ng/ml; and (ii) 13 post-menopausal women having a mean EGFR ECD value of $89.87 \pm 16.40$ ng/ml, with a range (mean$\pm 2$ SD) of from 57.07-122.67 ng/ml. For the control groups, the mean serum EGFR ECD level was significantly higher in post-menopausal females (i.e., $89.87 \pm 16.40$ ng/ml; n=13) compared with the mean EGFR ECD level in pre-menopausal females (i.e., $79.54 \pm 9.87$ ng/ml; n=46; p=0.006).

Analysis of the serum EGFR ECD values of the 265 post-menopausal cancer patients revealed a mean serum EGFR ECD level of 66.2 ng/ml, which was significantly lower than that of the post-menopausal female control group (p<0.00001). Using a cutoff point of 57.07 ng/ml (mean$\pm 2$ SD) form the post-menopausal female control group, 71/265 of the cancer patients (26.8%) had a decreased serum EGFR ECD level, compared to 0/13 of the controls.

The clinical benefit (i.e., CR+PR+Stable>24 weeks) was significantly less in patients with a decreased serum EGFR ECD level (p=0.04). Patients with decreased serum EGFR ECD levels had a shorter time to progression (TTP), (median 3.5 months) compared with patients with normal serum EGFR ECD levels (median 6.4 months), (p=0.04). In addition, the patients with decreased serum EGFR ECD levels (median 21.8 months) trended toward a shorter overall survival compared with patients with normal serum EGFR (27.8 months), (p=0.06). These results show that pretreatment serum EGFR ECD levels were significantly decreased in metastatic breast cancer patients compared with healthy controls, and patients with decreased serum EGFR ECD levels had reduced clinical benefit, TTP and overall survival compared with patients with normal serum EGFR ECD levels.

Example 4

Serial Analysis of EGFR ECD Levels in Sera from Prostate Cancer Patients

Serum samples were obtained from 25 prostate cancer patients. Each of the patients had from 4 to 6 serial blood samples drawn, from which the serum component was used. The serum samples were obtained in frozen form and were thawed prior to analysis by ELISA, as described in Example 1, for a determination of the levels of EGFR ECD over time. The samples were analyzed in a serial fashion on a monthly basis, or every two or three months, over a nine to twelve month period of time. Monitoring EGFR ECD levels in serum samples from patients taken over time in accordance with the methods of the present invention provides an advantageous approach to check and examine the patient's response to cancer therapy or treatment over an extended time period.

It will be appreciated that although, as exemplified here, the serum samples were frozen and then assayed at a later time, fresh blood samples can be collected from patients at the desired time intervals during the serial monitoring period, and the fresh serum (or plasma) samples used equally well for analysis of patient or treatment status and information according to this invention. Table 2 presents representative results of EGFR ECD levels determined from 5 prostate cancer patients whose serum samples were serially analyzed at six different time intervals during the monitoring period.

TABLE 2

| Patient/Sample No. | Draw Date | EGFR ECD ng/ml |
| --- | --- | --- |
| 3350-1 | April 2000 | 61.59 |
| 3350-2 | July 2000 | 77.66 |
| 3350-3 | August 2000 | 54.00 |
| 3350-4 | October 2000 | 39.03 |
| 3350-5 | November 2000 | 64.71 |
| 3350-6 | March 2001 | 57.81 |
| 3351-1 | June 2000 | 47.92 |
| 3351-2 | July 2000 | 73.31 |
| 3351-3 | August 2000 | 57.46 |
| 3351-4 | September 2000 | 40.21 |
| 3351-5 | November 2000 | 57.96 |
| 3351-6 | January 2001 | 55.29 |
| 3353-1 | December 1999 | 69.62 |
| 3353-2 | February 2000 | 52.75 |
| 3353-3 | April 2000 | 51.77 |
| 3353-4 | June 2000 | 52.07 |
| 3353-5 | August 2000 | 38.80 |
| 3353-6 | January 2001 | 31.56 |
| 3360-1 | June 2000 | 54.29 |
| 3360-2 | September 2000 | 50.65 |
| 3360-3 | December 2000 | 46.02 |
| 3360-4 | February 2001 | 42.92 |
| 3360-5 | March 2001 | 41.36 |
| 3360-6 | April 2001 | 58.03 |
| 3362-1 | March 2000 | 40.51 |
| 3362-2 | June 2000 | 39.24 |
| 3362-3 | August 2000 | 34.40 |
| 3362-4 | September 2000 | 34.52 |
| 3362-5 | November 2000 | 20.26 |
| 3362-6 | February 2001 | 75.98 |

Example 5

Analysis of EGFR ECD Levels and HER-2/Neu Levels, in Combination, in Sera from Breast Cancer Patients This Example describes the analysis and measurement of EGFR and HER-2/neu levels using ELISA protocols as described (Oncogene Science, Bayer Corporation, e.g., Example 1B). Pre-treatment sera were available from 265 metastatic breast cancer patients who participated in a trial of second line hormonal therapy. Further analysis was done by dividing the patients into the following 4 subgroups:
1) HER-2/neu normal and EGFR normal (n=135, 50.9%),
2) HER-2/neu normal and EGFR low (n=61, 23%),
3) HER-2/neu elevated and EGFR normal (n=46, 17.4%),
4) HER-2/neu elevated and EGFR low (n=23, 8.7%).

The clinical end points studied were clinical benefit rate (CBR) (i.e., CR+PR+stable disease>24 weeks), time to progression (TTP) and overall survival (OS). CBR was evaluated using a logistic regression model. TTP and OS were analyzed using the Cox proportional hazard model. P-values of less than 0.05 were considered statistically significant after correction for multiple comparisons.

Figure 4:
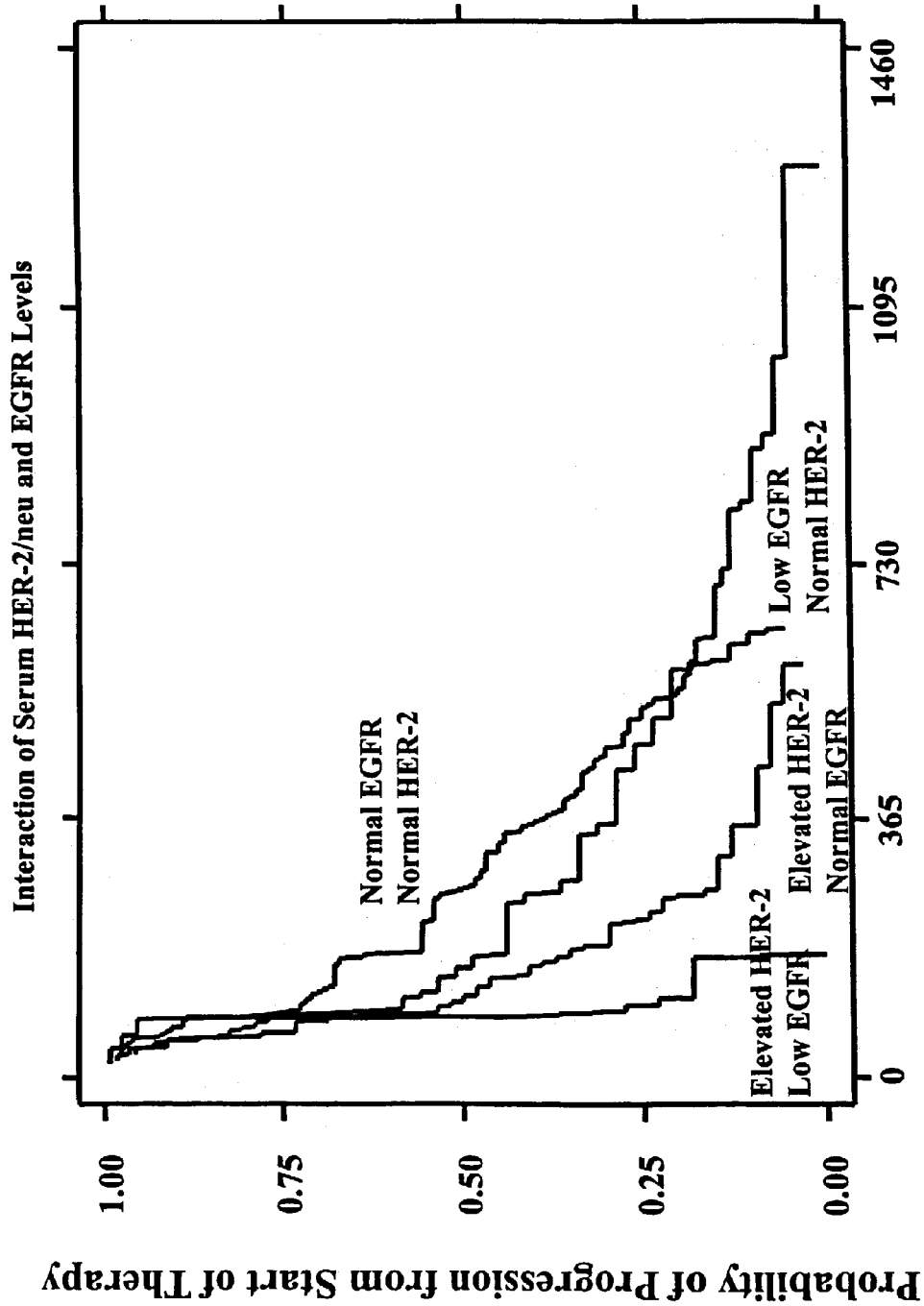
FIG. 4 depicts the time to progression of disease, based upon an assessment of the combination of serum EGFR and HER-2/neu levels in the sera of women with breast cancer.

When compared to patients with normal serum levels of HER-2/neu and EGFR (subgroup 1), patients with normal HER-2/neu and low EGFR (subgroup 2) were associated with a trend toward shorter survival (p=0.06). The subgroup of patients with high HER-2/neu levels and low EGFR levels (subgroup 4) also had a shorter TTP (p<0.0001) and overall survival (p<0.0001) when compared to patients with normal serum levels of HER-2/neu and EGFR (subgroup 1). (FIGS. 4 and 5).

The results of these analyses demonstrates that the analysis of a combination of serum HER-2/neu and EGFR levels allows the identification of subgroups of patients who have different predictive and prognostic outcomes for disease. Patients with elevated serum HER-2/neu and low serum EGFR levels (subgroup 4) were found to have the shortest TTP and survival. This group of patients would most likely benefit from combined EGFR- and HER-2/neu-directed therapies. The identification of a subgroup of patients with normal serum HER-2/neu and low EGFR levels (subgroup 2) would identify patients that are most likely to benefit from EGFR-directed therapy alone. Therefore this combined analysis and measurement provide important information for identifying patients for EGFR- and/or HER-2/neu-targeted therapies.

The contents of all issued and granted patents, patent applications, published PCT and U.S. applications, articles, books, references, reference manuals and abstracts as referenced or cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method of aiding in the prediction of overall patient survival in a breast cancer patient, comprising:
    (a) measuring the level of the extracellular domain (ECD) of the epidermal growth factor receptor (EGFR) in a serum or plasma sample of the breast cancer patient;

(b) measuring the level of the HER-2/neu receptor in the same serum or plasma sample of the breast cancer patient; and (c) determining, in combination, (i) if the level of the extracellular domain (ECD) of the epidermal growth factor receptor (EGFR) is decreased compared to the level of the extracellular domain (ECD) of the epidermal growth factor receptor (EGFR) in normal controls; and (ii) if the level of the HER-2/neu receptor is elevated compared to the level of HER-2/neu in normal controls;

wherein the normal range of the level of the extracellular domain (ECD) of the epidermal growth factor receptor (EGFR) in normal controls is about 45 to 78 ng/ml and the normal level of HER-2/neu in controls is less than about 15 ng/ml; and further wherein a decrease in the level of the extracellular domain (ECD) of the epidermal growth factor receptor (EGFR) compared to the level of the extracellular domain (ECD) of the epidermal growth factor receptor (EGFR) in normal controls and an elevation in the level of HER-2/neu compared to the level of HER-2/neu in normal controls in the breast cancer patient sample indicates the shorter overall survival for the patient.

2. The method according to claim 1, wherein the shorter overall survival is further associated with decreased EGFR LCD levels and elevated HER-2/neu levels in patients compared with controls having normal EGFR levels and elevated HER-2/neu levels; or controls having decreased EGFR levels and normal HER-2/levels.

3. The method according to claim 1, wherein the breast cancer patients have a solid tumor cancer.

4. The method according to claim 1, wherein the level of the extracellular domain (ECD) of the epidermal growth factor receptor (EGFR) is determined by an enzyme linked immunosorbent assay (ELISA) comprising antibodies immunoreactive with the extracellular domain (ECD) of the epidermal growth factor receptor (EGFR) and the level of HER-2/neu is determined by an enzyme linked immunosorbent assay (ELISA) comprising antibodies immunoreactive with HER-2/neu or the extracellular domain thereof.

5. A method to aid in the diagnostic and/or prognostic screening of a breast cancer patient, comprising:

(a) measuring the level of the extracellular domain (ECD) of the epidermal growth factor receptor (EGFR) in a serum or plasma sample of the breast cancer patient;

(b) measuring the level of the HER-2/neu receptor in the same serum or plasma sample of the breast cancer patient;

(c) determining, in combination, (i) if the level of the extracellular domain (ECD) of the epidermal growth factor receptor (EGFR) is decreased compared to the level of the extracellular domain (ECD) of the epidermal growth factor receptor (EGFR) in normal controls; and (ii) if the level of the HER-2/neu receptor is elevated compared to the level of HER-2/neu in normal controls;

wherein the normal range of the level of the extracellular domain (ECD) of the epidermal growth factor receptor (EGFR) in normal controls is about 45 to 78 ng/ml and the normal level of HER-2/neu in controls is less than about 15 ng/ml; and further wherein a decrease in the level of the extracellular domain (ECD) of the epidermal growth factor receptor (EGFR) compared to the level of the extracellular domain (ECD) of the epidermal growth factor receptor (EGFR) in normal controls and an elevation in the level of HER-2/neu compared to the level of HER-2/neu in normal controls in the patient sample indicates the shorter overall survival for the patient.

6. A method to aid in the diagnostic and/or prognostic screening of a breast cancer patient, comprising:

(a) measuring the level of the extracellular domain (ECD) of the epidermal growth factor receptor (EGFR) in a serum or plasma sample of the breast cancer patient;

(b) measuring the level of the HER-2/neu receptor in the same serum or plasma sample of the breast cancer patient;

(c) determining, in combination, (i) if the level of the extracellular domain (ECD) of the epidermal growth factor receptor (EGFR) is decreased compared to the level of the extracellular domain (ECD) of the epidermal growth factor receptor (EGFR) in normal controls; and (ii) if the level of the HER-2/neu receptor is elevated compared to the level of HER-2/neu in normal controls wherein a decrease in the level of the extracellular domain (ECD) of the epidermal growth factor receptor (EGFR) compared to the level of the extracellular domain (ECD) of epidermal growth factor receptor (EGFR) in normal controls, and an elevation in the level of HER-2/neu compared to the level of HER-2/neu in normal controls in the patient sample indicates the shorter overall survival for the patient.

7. The method according to claim 6, wherein the normal range of the level of the extracellular domain (ECD) of the epidermal growth factor receptor (EGFR) in normal controls is about 45 to 78 ng/ml and the normal level of HER-2/neu in controls is less than about 15 ng/ml.

8. The method according to claim 5, wherein the shorter overall survival is further associated with decreased EGFR LCD levels and elevated HER-2/neu levels in patients compared with controls having normal EGFR levels and elevated HER-2/neu levels; or controls having decreased EGFR levels and normal HER-2/levels.

9. The method according to claim 5, wherein the breast cancer patients have a solid tumor cancer.

* * * * *